(12) United States Patent
Mano et al.

(10) Patent No.: US 9,200,308 B2
(45) Date of Patent: Dec. 1, 2015

(54) *PENICILLIUM AMAGASAKIENSE* GLUCOSE OXIDASE MUTANTS

(75) Inventors: Nicolas Mano, Talence (FR); Olivier Courjean, Bordeaux (FR); Emilie Tremey, Talence (FR); Sébastien Gounel, Berthez (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 107 days.

(21) Appl. No.: 14/343,684

(22) PCT Filed: Sep. 7, 2012

(86) PCT No.: PCT/IB2012/054650
§ 371 (c)(1),
(2), (4) Date: May 1, 2014

(87) PCT Pub. No.: WO2013/035080
PCT Pub. Date: Mar. 14, 2013

(65) Prior Publication Data
US 2014/0305809 A1  Oct. 16, 2014

(30) Foreign Application Priority Data
Sep. 8, 2011  (FR) ...................................... 11 57979

(51) Int. Cl.
| | | |
|---|---|---|
| *C12Q 1/00* | (2006.01) | |
| *C12M 1/00* | (2006.01) | |
| *C12N 9/04* | (2006.01) | |
| *C12P 19/34* | (2006.01) | |
| *C12N 15/00* | (2006.01) | |
| *C12N 1/20* | (2006.01) | |
| *C07H 21/04* | (2006.01) | |
| *C07K 1/00* | (2006.01) | |

(52) U.S. Cl.
CPC .............. *C12Q 1/006* (2013.01); *C12N 9/0006* (2013.01); *C12Y 101/03004* (2013.01)

(58) Field of Classification Search
CPC ..................... C12Y 101/03004; C12N 9/0006; C12Q 1/006
USPC ............ 205/777.5; 204/403.4; 435/190, 69.1, 435/91.1, 320.1, 252.3; 536/23.1, 23.2; 530/350
See application file for complete search history.

(56) References Cited

U.S. PATENT DOCUMENTS
2012/0244565 A1    9/2012  Nishio et al.

OTHER PUBLICATIONS

International Search Report for PCT/IB2012/054650 dated Nov. 29, 2012.
Written Opinion of the International Searching Authority for PCT/IB2012/054650 dated Nov. 29, 2012.
Sandip B Bankar et al: "Glucose oxidase—An overview", Biotechnology Advances, Elsevier Publishing, Barking, GB, vol. 27, No. 4, (Jul. 1, 2009), pp. 489-501.

*Primary Examiner* — Ganapathirama Raghu
(74) *Attorney, Agent, or Firm* — B. Aaron Schulman, Esq.; Stites & Harbison, PLLC.

(57) ABSTRACT

The present invention relates to mutants of the *Penicillium amagasakiense* glucose oxidase (GOx) enzyme which are of use for assaying glucose and to the development in particular of glucose electrodes and of biocells which use glucose as fuel.

16 Claims, 4 Drawing Sheets

PENICILLIUM AMAGASAKIENSE GLUCOSE OXIDASE MUTANTS

The present invention relates to the field of developing glucose electrodes which are of interest in assaying glucose, in particular the blood glucose of diabetic individuals, and for the use of biocells using glucose as fuel.

The present invention is more particularly directed toward mutants of the glucose oxidase enzyme (also referred to hereinbelow as GOx) of *Penicillium amagasakiense* which have advantageous properties over the wild-type enzymes, in particular the commercialized enzymes.

Type-2 diabetes affects nearly two million people in France, added to which are 600 000 people who are unaware of their disease. In the United States, the situation is even more critical. In developed countries, diabetes is the main cause of blindness among 20-65 year olds.

The monitoring and surveillance of the disease is based, inter alia, on daily assay of the blood glucose and the injection of insulin. Various companies propose glucose sensors that enable patients to measure their glycemia at home. These sensors may be amperometric, potentiometric or coulometric; they are all based on the use of an enzyme that is capable of oxidizing glucose; the two main enzymes being glucose oxidase and PQQ s-GDH.

Glucose oxidase (also referred to hereinbelow as GOx) is an oxidoreductase enzyme (EC 1.1.3.4) which catalyzes the oxidation of glucose to hydrogen peroxide and D-glucono-δ-lactone according to the following reaction scheme:

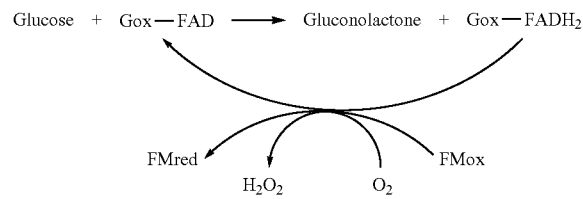

Glucose oxidase was isolated for the first time from *Aspergillus niger*; the GOx most conventionally produced are those from *Penicilium chrysogenum*, *Penicillium glaucum*, *Penicillium purpurogenum*, *Penicillium amagasakiense*, *Aspergillus niger* and *Aspergillus fumaricus*.

The marketed GOx are usually those from *Aspergillus niger* and *Penicillium amagasakiense*; they are mainly used in the food industry, especially for conservation purposes as a source of hydrogen peroxide. They are also used for assaying glucose or in glucose biocells. These two enzymes were especially studied and compared in the article by Wohlfahart et al. (Acta. Cryst (1999) D55, 969-977).

As regards GOx from *Penicillium amagasakiense*, Witt et al. described its cloning and its expression with *Escherichia coli* (Applied and Environmental Microbiology (1998) vol. 64, No. 4, 1405-1411).

The drawback of the currently available glucose oxidases is their sensitivity to $O_2$ which participates as an electron acceptor in the reaction catalyzed by GOx. Specifically, oxygen is the natural cofactor of GOx and enables their reoxidation after the oxidation of glucose. During the use of these enzymes in glucose sensors, there is thus competition for recovery of the electrons from the enzyme between oxygen and the redox mediators which provide the electrical connection of the enzyme to the surface of the electrodes.

In addition, for their use in glucose sensors, it is necessary to have available more active GOx mutants, i.e. mutants which allow a faster transformation reaction of glucose to D-gluconolactone than with the existing enzymes.

It thus remains necessary to improve the properties of the existing GOx.

This is what the Inventors have managed to do by developing novel mutants of the wild-type GOx of *Penicillium amagasakiense*.

The term "mutant or variant" means a GOx whose protein sequence comprises the insertion, deletion and/or replacement of at least one amino acid relative to the protein sequence of the wild-type GOx; hereinbelow, the reference nucleotide and protein sequences of GOx are those of the wild-type GOx of *Penicillium amagasakiense* (respectively SEQ. ID. No. 1 and 2).

The mutants according to the present invention are such that the valine in position 564 is replaced with a serine (V564S mutant), a threonine (V564T mutant) or an isoleucine (V564I mutant); when said valine is replaced with a serine, the mutants such that the lysine in position 424 is replaced with a glutamic acid, glutamine, methionine and leucine are also subjects of the present invention (V564S+K424E, V564S+K424Q, V564S+K424M and V564S+K424L mutants, respectively).

Thus, a first subject of the invention relates to a GOx mutant with a percentage of identity of at least 80%, and, in order of increasing preference, at least 85%, 90%, 95%, 97%, 98% and 99%, relative to the wild-type GOx of *Penicillium amagasakiense*, characterized in that its amino acid in position 564, with reference to the protein sequence of the wild-type GOx of *Penicillium amagasakiense* (SEQ. ID. No. 2), is replaced with an amino acid selected from the group consisting of a serine (V564S mutant), a threonine (V564T mutant) or an isoleucine (V564I mutant).

According to a particular variant, the V564S mutant also comprises a replacement of the lysine in position 424 with a glutamic acid, glutamine, methionine or leucine (V564S+K424E, V564S+K424Q, V564S+K424M and V564S+K424L mutants, respectively).

The numbering of the amino acids refers to the sequence of the wild-type GOx of *Penicillium amagasakiense*.

The identity of a sequence relative to the sequence of the wild-type GOx of *Penicillium amagasakiense* (SEQ. ID. No. 2) as reference sequence is assessed as a function of the percentage of amino acid residues that are identical, when the two sequences are aligned, so as to obtain the maximum correspondence between them.

The percentage of identity may be calculated by a person skilled in the art using a computer program for comparing sequences, for instance the BLAST software (Altschul et al., NAR, 25, 3389-3402). The BLAST programs are used on the comparison window consisting of all of the SEQ. ID. No. 2 indicated as the reference sequence.

A peptide with an amino acid sequence having at least X % identity with a reference sequence is defined in the present invention as a peptide whose sequence may include up to 100-X alterations per 100 amino acids of the reference sequence, while conserving the functional properties of said reference peptide, in the present case its enzymatic activity for the oxidation of glucose. For the purposes of the present invention, the term "alteration" includes consecutive or dispersed deletions, replacements or insertions of amino acids in the reference sequence.

The amino acid corresponding to the amino acid in position 564 of the wild-type GOx of *Penicillium amagasakiense* is identified by aligning the sequence of said homologous enzyme with the GOx of *Penicillium amagasakiense*.

A particular subject of the invention relates to a GOx mutant with an amino acid sequence chosen from SEQ. ID. No. 4, 6, 8, 10, 22, 24 and 26 corresponding, respectively, to the amino acid sequences of the mutants V564S, V564T, V564I, V564+K424E, V564S+K424Q, V564S+KL424M and V564S+K424L of GOx; these mutated enzymes are encoded by nucleotide fragments obtained by mutation of the wild-type GOx gene of *Penicillium amagasakiense* with adapted pairs of oligonucleotides.

These novel GOx mutants according to the invention have improved performance qualities over the wild-type enzyme of *Aspergillus niger* which is the enzyme used in commercial glucose sensors.

More particularly, the improved properties of the mutants according to the invention lie in a reduced sensitivity to oxygen: in solution in the presence of 1 mM of glucose and in air, the mutants are 17 times less sensitive to oxygen than the GOx of *A. niger*. Once adsorbed onto the surface of electrodes, under 1 atm of $O_2$ and at 1 mM of glucose, the mutants are 70% less sensitive to $O_2$.

The advantageous properties of the GOx mutants according to the invention make their use particularly suited to bioelectric systems such as biocells using glucose as a source of energy and glucose biosensors.

The present invention also relates to a nucleic acid molecule coding for a GOx mutant according to the invention; said nucleic acid molecule being obtained by modification of a wild-type GOx, such as that of *Penicillium amagasakiense*, with an oligonucleotide pair selected from the group consisting of the oligonucleotide pairs represented in Table I.

TABLE I sequence listing of the oligonucleotides used for the preparation of the GOx mutants according to the invention

| Oligo-nucleotides | Sequences |
|---|---|
| Oligonucleotide pair corresponding to the wild-type enzyme | |
| Sense | 5'-g gtg tct tcc cat gtc atg acc att ttc tac gg-3' (SEQ. ID. No. 11) |
| Antisense | 5'-cc gta gaa aat ggt cat gac atg gga aga cac c-3' (SEQ. ID. No. 12) |
| Oligonucleotide pair used for the preparation of the V564S mutant | |
| Sense | 5'-g gtg tct tcc cat tcc atg acc att ttc tac gg-3' (SEQ. ID. No. 13) |
| Antisense | 5'-cc gta gaa aat ggt cat gga atg gga aga cac c-3' (SEQ. ID. No. 14) |
| Oligonucleotide pair used for the preparation of the V564T mutant | |
| Sense | 5'-g gtg tct tcc cat acc atg acc att ttc tac gg-3' (SEQ. ID. NO. 15) |
| Antisense | 5'-cc gta gaa aat ggt cat ggt atg gga aga cac c-3' (SEQ. ID. No. 16) |

TABLE I-continued sequence listing of the oligonucleotides used for the preparation of the GOx mutants according to the invention

| Oligo-nucleotides | Sequences |
|---|---|
| Oligonucleotide pair used for the preparation of the V564I mutant | |
| Sense | 5'-g gtg tct tcc cat att atg acc att ttc tac gg-3' (SEQ. ID. NO. 17) |
| Antisense | 5'-cc gta gaa aat ggt cat aat atg gga aga cac c-3' (SEQ. ID. No. 18) |
| Oligonucleotide pair used for the preparation of the K424E mutatation of the V564S-K424E mutant (this mutation is performed after the V564S mutation) | |
| Sense | 5'-ggacaccgagggcgagatcaacttcg-3' (SEQ. ID. No. 19) |
| Antisense | 5'-cgaagttgatctcgccctcggtgtcc-3' (SEQ. ID. No. 20) |
| Oligonucleotide pair used for the preparation of the K424Q mutatation of the V564S-K424Q mutant (this mutation is performed after the V564S mutation) | |
| Sense | 5'-ggacaccgagggccagatcaacttcgat ttatg-3' (SEQ. ID. No. 27) |
| Antisense | 5'-cataaatcgaagttgatctggccctcgg tgtcc-3' (SEQ. ID. No. 28) |
| Oligonucleotide pair used for the preparation of the K424M mutatation of the V564S-K424M mutant (this mutation is performed after the V564S mutation) | |
| Sense | 5'-ggacaccgagggcatgatcaacttcgat ttatg-3' (SEQ. ID. No. 29) |
| Antisense | 5'-cataaatcgaagttgatcatgccctcgg tgtcc-3' (SEQ. ID. No. 30) |
| Oligonucleotide pair used for the preparation of the K424L mutatation of the V564S-K424L mutant (this mutation is performed after the V564S mutation) | |
| Sense | 5'-ggacaccgagggcttgatcaacttcgat ttatg-3' (SEQ. ID. No. 31) |
| Antisense | 5'-cataaatcgaagttgatcaagccctcgg tgtcc-3' (SEQ. ID. No. 32) |

The nucleic acid molecules coding for the GOx mutants according to the invention may especially be prepared by modifying the nucleotide sequence of the gene coding for the wild-type enzyme of sequence SEQ. ID. No. 1 produced by *Penicillium amagasakiense*. Several techniques for modifying the gene sequence are known to those skilled in the art (see the review by Igarashi et al., Archives of Biochemistry and Biophysocs 428 (2004) 52-63). In a particular mode of preparation, the nucleic acid molecules coding for the GOx mutants according to the invention are prepared by mutagenesis by PCR in the presence of an oligonucleotide bearing the mutation to be introduced (see the experimental section, point 2.5 below).

According to a particular embodiment, the present invention relates to a nucleic acid molecule coding for a GOx mutant according to the invention whose sequence is selected from the group consisting of sequences SEQ. ID. No. 3, 5, 7, 9, 21, 23 and 25. The nucleic acid molecules coding for the GOx mutants according to the invention may then be cloned in an expression vector such as a plasmid, and then transformed in a suitable host such as a bacterium, a yeast or a cell culture.

The term "expression vector" means a vector bearing a region for insertion of a coding nucleotide sequence between the signals that are essential for its expression, especially a promoter (constitutive or inducible), a ribosome binding site, a transcription termination signal, and, optionally, a selection marker such as a gene for resistance to an antibiotic.

The present invention also relates to an expression vector comprising said nucleic acid molecule and to a host cell transformed with said expression vector and expressing a GOx mutant according to the invention.

The introduction of the expression vector into the host cell may be performed via any method known to those skilled in the art, in particular by modification of the membrane permeability of the host cell, for example in the presence of calcium ions, or by electroporation.

After culturing the transformed host cells to express a GOx mutant according to the invention, said cells may be recovered by centrifugation, lyzed so as to release the enzymes including said GOx mutant according to the invention.

If *Escherichia coli* is the host microorganism, the plasmids that may be used are especially the plasmids pET24a, pBluescript, pUC18 or the like.

By way of example, the host cells that may be used comprise *Escherichia coli* $BL_{21}$, *Escherichia coli* W3110, *Escherichia coli* C600, *Escherichia coli* JM109, *Escherichia coli* JM101, *Escherichia coli* DH5α, etc.

Preferably, the GOx mutants according to the invention are produced in a strain of *Escherichia coli* $BL_{21}$; the nucleic acid molecule which codes them is obtained by modification of the GOx gene of *Penicillium amagasakiense* and cloned in the vector pET24a. The mutants thus produced are exported into the periplasm of the bacterium by means of the signal sequence of GOx. The mutants thus produced are exported in the inclusion bodies of the bacterium. The mutants are then purified after rupturing the bacteria by cell lysis in the presence of 8M urea.

The invention also relates to the use of a GOx mutant according to the invention for assaying glucose in solution, i.e. for measuring the concentration of glucose in a sample, especially a biological sample, in particular in blood.

The assay of glucose in solution in a given biological sample may be performed by introducing into said sample a redox reagent and a GOx mutant according to the invention and then by comparing the intensity of the coloration obtained with standard solutions having a known glucose content.

The present invention also relates to a kit for assaying a glucose solution, characterized in that it comprises a GOx mutant according to the invention.

Typically, said assay kit also contains the reagents necessary for performing the glucose assay test, in particular buffers; any buffer may be used in the kit according to the invention, mention may be made without any limiting nature of phosphate or acetate buffers, tris(hydroxymethyl)aminomethane (TRIS) buffer, N-morpholino-3-propanesulfonic acid (MPOS), 4-(2-hydroxyethyl)-1-piperazineethanesulfonic acid (HEPES), buffer comprising a mixture of buffers such as TRIS-acetate, etc., the redox reagents may be any reagent that allows the GOx mutant to be oxidized, and may be selected from the group consisting of phenazine methosulfate (PMS) in combination with 2,6-dichlorophenolindophenol (DCIP); potassium ferricyanide; ferrocene and ferrocene-based complexes such as ferrocenemethanol, ferrocenecarboxylic acid; and osmium and ruthenium complexes, standard glucose solutions for preparing calibration curves, and the necessary instructions for use for performing the assay.

The present invention also relates to glucose electrodes comprising a conductive material such as a conductive metal, especially platinum, copper, silver, aluminum, gold or carbon steel, such as vitreous carbon, carbon fibers, carbon nanotube fibers or diamond, etc., said conductive material is covered with a deposit comprising at least one GOx mutant according to the invention; said deposit also possibly comprising a redox polymer to improve the conductive properties of the conductive material.

The redox polymer is chosen from polymers based on ferrocene, osmium and ruthenium and conductive polymers such as polypyrrole and polyaniline.

The methods for immobilizing the GOx mutant on said conductive material may be chosen from the standard methods available to a person skilled in the art, which especially comprise inclusion of the GOx mutant in a polymer matrix, adsorption of the GOx mutant onto the surface of the polymer membrane, binding by covalent bonding or alternatively electrodeposition (Gao et al., Chem. Int. ED. 2002, 41, No. 5, 810-813).

Such electrodes are advantageously used in bioelectrical systems such as glucose biocells or glucose biosensors.

The present invention thus also relates to a glucose biosensor comprising an electrode according to the invention.

A glucose biosensor consists of an electrode on which is immobilized a bioreceptor that is capable of recognizing a biological target; the binding of the biological target to the bioreceptor leads to physicochemical modifications of the membrane and the production of an electrical signal via an electrochemical transducer (amperometric, potentiometric, conductimetric, etc.) attached to the electrode; in the present case, the bioreceptor is a GOx mutant according to the invention and the biological target is its substrate: glucose.

According to an embodiment variant, the electrode on which is immobilized the GOx mutant is also covered with a membrane which prevents detachment of said mutant from the electrode. Said membrane may consist of nafium, cellulose or any biocompatible material, i.e. any material that is compatible with a physiological environment.

According to a variant of the invention, the glucose biosensor is implanted under the skin and allows the glucose concentration of the blood to be recorded.

The present invention also relates to biocells using glucose as a source of energy and comprising a first electrode according to the invention as anode and a second electrode as cathode. The cathode may be, for example, an enzymatic electrode for reducing oxygen, bearing an enzyme chosen from the class of copper-based enzymes (multicopper oxidases) and particularly bilirubine oxidase and laccase. It may also be a metal electrode, for example made of platinum, gold or a platinum or gold alloy.

FIG. 1 more specifically illustrates an enzymatic glucose biocell; such an enzymatic biocell consists of two electrodes modified by immobilization of enzymes. A glucose oxidase (GOx) is attached to the anode (1) via a conductive polymer "I" and a bilirubine oxidase (BOD) is attached to the cathode (2) via a conductive polymer "II". When functioning, at the anode, the electrons are transferred from the glucose present in the physiological fluid to the GOx, and then from the GOx to the conductive polymer "I" and from the conductive polymer "I" to the anode. At the cathode, the electrons are transferred from the cathode to the conductive polymer "II" and then to the BOD and finally from the BOD to the oxygen present in the physiological fluid.

It should be noted that a biocell may also optionally function by modifying the electrodes with their respective enzymes and by adding soluble mediators, such as ferrocenemethanol for the anode and potassium ferricyanide for the cathode, and by adding, where appropriate, a membrane separating the anode and the cathode.

The invention also relates to a process for assaying glucose in solution in a sample, comprising the following steps:
a) introduction into said sample of a redox reagent whose reduction leads to a color change and of a GOx mutant according to the invention;
b) measurement of the coloration intensity of the sample after enzymatic reaction;
c) comparison of the coloration intensity measured in step b) with the intensity measured for standard solutions having a known glucose content;
d) determination of the glucose concentration of said sample.

The redox reagent whose reduction leads to a color change is chosen from phenazinemethosulfate (PMS) in combination with 2,6-dichlorophenolindophenol (DCIP), potassium ferricyanide and ferrocene.

The invention also relates to a process for assaying the glucose of a sample, characterized in that it comprises the following steps:
a) introduction into said sample of a glucose electrode according to the invention;
b) measurement of the intensity of the current in the sample;
c) comparison of the intensity of the current measured in step b) with the intensity measured for standard solutions having a known glucose content;
d) determination of the glucose concentration of said sample.

Besides the preceding arrangements, the invention also comprises other arrangements that will emerge from the description that follows, which refer to examples of implementation of the present invention, and also to the attached figures, in which:

FIGURES

FIG. 1 schematically represents a biocell.

1. MATERIALS

1.1 Bacterial Strains of *Escherichia coli*

$DH_5\alpha$:supE44, ΔlacU169, (Φ80 lacZDM15), hsdR17, recA1, endA1, gyrA96, thi-1, relA1 (Hanahan, 1983). This strain is used for the amplification of the plasmid during the steps of construction of the protein expression vectors. $BL_{21}$: F– ompT hsdSB(rB–, mB–) gal dcm (DE3) (Invitrogen). This strain is used for the production in conical flasks of GOx from *Penicillium amagasakiense* (penag). This strain is then transformed by the plasmid pET24a which contains the DNA sequence coding for the GOx of *Penicillium amagasakiense* under the dependence of the T7 promoter in the vector pET24a.

Figure 1:
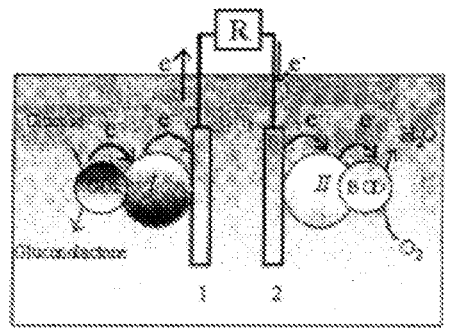
Figure 2:
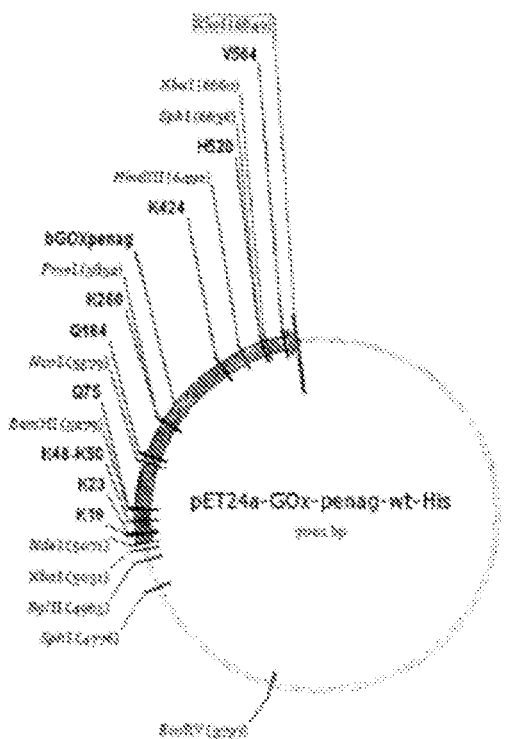
FIG. 2 represents the plasmid map of the vector pET24a-GOx-penag-wt-His.

1.2 Vector pET24a: plasmid pET24a containing the DNA sequence coding for the GOx of *Penicillium amagasakiense* cloned in phase with the C-terminal 6xHis label (the map of this plasmid is represented in FIG. 2).

1.3 Culture Medium

LB-rich medium:
Tryptone 10 g/l
Yeast extract 5 g/l
NaCl 5 g/l
Distilled $H_2O$ qsp 1 L
pH not adjusted, autoclaved for 50 minutes at 1 bar.

2. GENETIC ENGINEERING TECHNIQUES

2.1 Preparation of the Electrocompetent Bacteria 5 ml of $DH_5\alpha$ cell preculture are inoculated in 1 L of LB and are cultured at 37° C. up to the exponential phase (OD between 0.6 and 0.8). The cells thus harvested by centrifugation at 4000 g are successively washed with cold milliQ® water until 2 ml of cells that have become electrocompetent are obtained.

2.2 Transformation of the Electrocompetent Bacteria

1 µl of plasmid DNA is incorporated into 40 µl of electrocompetent cells, placed in an electroporation tank and immediately transformed by the electroporator. 500 µl of SOC (culture medium containing 2% tryptone, 0.5% yeast extract, 10 mM NaCl, 2.5 mM KCl, 10 mM $MgCl_2$, 10 mM $MgSO_4$) are added, incubated for 5 minutes in ice and cultured for 1 hour at 37° C. The 500 µl of cultures are then deposited in an LB-agar dish and incubated overnight at 37° C.

2.3 Preparation of the DNA

This step is performed using the QIAprep® Miniprep kit (Qiagen) which makes it possible to extract and purify the plasmid DNA from 10 ml of culture of $DH_5\alpha$ cells transformed with the desired plasmid. After collecting the cells by centrifugation, they undergo alkaline lysis, in the presence of RNase, and also a precipitation of the genomic DNA with acetic acid. The DNA is then removed by centrifugation and the supernatant deposited on a column comprising a silica matrix, allowing selective adsorption of the plasmid DNA in the presence of a strong concentration of salt. After washing with ethanol to remove the salts, the RNA and the protein, the plasmid DNA is eluted with a buffer of weak ionic strength (water or buffer: Tris-HCl 10 mM pH 8.5). The DNA thus purified may be quantified by UV-visible spectrometry at 260 nm. An absorbance of 1 corresponds to a DNA concentration of 50 ng·µl$^{-1}$. The purified plasmid DNA is stored at –20° C.

2.4 Digestion of the DNA

For total digestion, 200 to 500 ng of plasmid DNA are digested with 0.5 µl of XbaI restriction enzyme in the appropriate reaction buffer, in a final volume of 15 µl. The reaction takes place at 37° C. for 1 hour.

2.5 PCR-directed Mutagenesis

The GOx mutants V564I, V564S, V564T and V564S+K424E are obtained by directed mutagenesis. This method requires the use of a double-stranded plasmid (plasmid pET24a) bearing the gene of interest (GOx) and also 2 synthetic oligonucleotides whose sequence is complementary to the DNA strand to be modified, with the exception of the desired mutation. These oligonucleotides contain between and 45 bases, with a melting point (Tm) of greater than or equal to 70° C.

$$Tm=81.5+0.41\,(\%\,GC)-675/N-\%\,(\text{not paired})$$

With N the number of bases in the sequence, % GC the percentage of G and C bases in the sequence and % (not paired) the number of mutated bases (zero value in the case of deletion or insertion of a base). The chosen sequence must contain at least 40% of GC bases and must terminate with a C or a G.

The sequences of the oligonucleotides used are presented in table I above.

10 ng of parental plasmid, 12.5 ng of each of the primers, 1 µl of a mixture of 10 mM concentrated dNTP, 5 µl of reaction buffer, 1 µl of Pfu Turbo DNA polymerase (2.5 U·µl$^{-1}$) and 50 µl qs of sterile water are mixed in a sterile Eppendorf flask.

The mutagenesis is performed via a sequence of temperature cycles performed automatically by a thermocycler. Each cycle comprises three steps. In a first stage, the 2 strands of the matrix DNA are separated by thermal denaturing, the oligonucleotides are then paired with their complementary sequence on the matrix DNA. They serve as primers for the elongation step, during which PfuTurbo polymerase (a heat-resistant DNA polymerase) synthesizes the DNA complementary to the parental strand.

Once this sequence of cycles is complete, the reaction product is treated with Dpn I, an endonuclease which specifically digests the methylated and hemimethylated DNA of the parental plasmid. The mutated DNA is finally introduced into competent cells which link the ends of the plasmid that are still free after the DNA synthesis.

2.6 Sequencing of the Double-stranded DNA

The double-stranded DNA is sequenced with the genomics platform of the université Victor Segalen. The sequence reactions are performed with the BigDye Terminator v.1.1 or v3.1 sequencing kit. The reagent contains the four ddNTPs with different fluorescent markers (BigDye Terminators), AmpliTaq DNA polymerase, and all the other components necessary for the reaction. The extension products must be purified before passage on the ABI 3130x1 sequencer, to remove the markers not incorporated, salts and other contaminants.

3. Production And Purification of The Glucose Oxidase Enzyme Of *Penicillium Amagasakiense*

3.1 Production of the Wild-type and Mutated GOx Enzymes

The GOx enzyme is produced in the strain *E. coli* BL21 via the recombinant plasmid pET24a bearing the sequence coding for the wild-type or mutated GOx. A preculture of 2 ml of LB medium supplemented with kanamycin (1×) is seeded with an isolated clone on an LB agar dish supplemented with kanamycin (1×) and left stirring at 220 rpm overnight at 37° C. A 50 ml culture is then seeded at 1/25 in LB medium supplemented with kanamycin (1×) in a 250 ml conical flask. This flask is incubated at 37° C. with stirring (220 rpm) to an $OD_{600\,nm}$ of between 0.8 and 1 $OD_{600\,nm}$/ml. The culture is then induced with 500 µM of IPTG and then left stirring (220 rpm) at 37° C. for 2 hours.

3.2 Preparation of the Soluble Extracts

The cells harvested by centrifugation (4500 g, 4° C.) are first washed in 5 ml of Tris/HCl 20 mM buffer; NaCl 100 mM; EDTA 1 mM. The cells harvested by centrifugation (4500 g, 4° C.) are then washed in 5 ml of Tris/HCl 20 mM buffer; NaCl 100 mM; EDTA 1 mM containing 3 M urea in order to embrittle the cell membrane. The harvested cells (4500 g, 4° C.) are incubated for 1 hour on ice in the presence of 5 ml of Tris/HCl 20 mM buffer; NaCl 100 mM; EDTA 1 mM containing 8M urea allowing complete lysis of the cells. The supernatant is harvested after centrifugation at 4500 g at 4° C. and then stored at −20° C.

3.3 Reconstitution of the GOx

In the bacterium *E. coli* BL21, glucose oxidase from *Penicillium amagasakiense* is overexpressed in its Apo form, i.e. in the absence of its cofactor flavine adenine dinucleotide (FAD). It is thus necessary to reconstitute it chemically. To do this, the 5 ml of soluble extract obtained are added dropwise with vigorous stirring, so as to avoid the precipitation of the protein, to 500 ml of a reconstitution solution containing 10% glycerol, 1 mM of reduced glutathione, 1 mM of oxidized glutathione, 100 µM of FAD in Tris/HCl 20 mM pH 8 buffer. This solution is stored for 5 days at 4° C. protected from light.

3.4 Purification of the GOx

Anion-exchange Chromatography

The reconstitution solution, dialyzed in 20 mM pH 6 acetate buffer to allow precipitation of the remaining Apo form, is concentrated to 5 ml on an Amicon YM10 membrane and then filtered through a 0.22 µm filter. This solution is injected onto a QFF anion-exchange column (GE Healthcare®), coupled to the AKTA purifier system (GE Healthcare®) equilibrated in a 20 mM pH 6 sodium acetate buffer. The elution is performed with a gradient of from 0% to 30% of a 50 mM sodium acetate, 250 mM NaCl, pH 3 buffer at a flow rate of 1 ml/min. The fractions containing the GOx protein are identified by an ABTS activity test and are combined, concentrated and desalified with a 100 mM pH 5 phosphate buffer by centrifugation on an Amicon YM10 membrane. At this stage, the GOx protein is pure and can be stored at 4° C. in soluble form.

4. Characterization of the wild-type and mutated gox Enzymes

4.1 Measurement of the Concentration

The protein concentration determination is performed by UV-visible spectroscopy using a Varian spectrophotometer in a 100 mM pH 5 phosphate buffer at 25° C. The purified GOx proteins have a characteristic spectrum between 200 and 800 nm. The first band at 280 nm is characteristic of the absorption of the aromatic amino acids and makes it possible to obtain the enzyme concentration ($\epsilon$=263 mM$^{-1}$·cm$^{-1}$). The other two bands at 380 and 461 nm are characteristic of the FAD integrated into the protein.

The absorbance value at 461 nm makes it possible to obtain the concentration of cofactor present in the protein ($\epsilon$=12.83 mM$^{-1}$·cm$^{-1}$). The ratio between the GOx concentration and the FAD concentration is equal to 2 when the protein is completely reconstituted.

4.2 Enzymatic Test

The enzymatic tests are performed by UV-visible spectroscopy using a Varian spectrophotometer in air.

The enzymatic tests are performed in the presence of a strong excess of glucose (150 mM) so as to be able to observe only the reoxidation of GOx by the mediators.

Two enzymatic tests are performed. The first with an ABTS-HRP mixture (2,2'-azinobis(3-ethylbenzthiazoline-6-sulfonic acid)-horseradish peroxidase) to be able to observe the reoxidation with oxygen. The ABTS is oxidized in the presence of HRP and $H_2O_2$. And the second with oxidized ferrocenemethanol, so as to be able to observe the reoxidation of the GOx by a redox mediator having a redox potential close to that used in electrochemistry.

4.2.1 ABTS-HRP Enzymatic Test

The tests are performed in a 100 mM pH 5 phosphate buffer at 37° C. in a volume of 3 ml containing 100 µl of HRP (60 U/ml), 24 µL of ABTS (11.5 mg/ml) and 150 mM of glucose. The ABTS oxidation is monitored at 405 nm as a function of time (ε=36.8 mM$^{-1}$·cm$^{-1}$). The specific activity of the enzyme is expressed as micromoles of product appeared per mg of enzyme (U/mg). The enzyme is diluted to 50 nM so as to measure a slope of between 0.05 and 0.3 OD$_{405\,nm}$/min.

4.2.2 Ferrocenemethanol Enzymatic Test (FMox)

4.2.2.1 Preparation of the Ferrocenemethanol

Commercial ferrocenemethanol is in reduced form, and it is thus necessary to oxidize it in order to be able to use it in the enzymatic tests. To do this, 100 mg of reduced ferrocenemethanol are dissolved in 50 ml of 50 mM pH 7.5 phosphate buffer and placed in an electrolysis cell comprising a working electrode (carbon electrode), an Ag/AgCl reference electrode, a platinum counterelectrode placed in a sinter containing 50 mM pH 7.5 phosphate buffer. The system is under argon. The electrolysis is performed at 0.5 V for 4 hours.

4.2.2.2 Enzymatic Test

Figure 3:
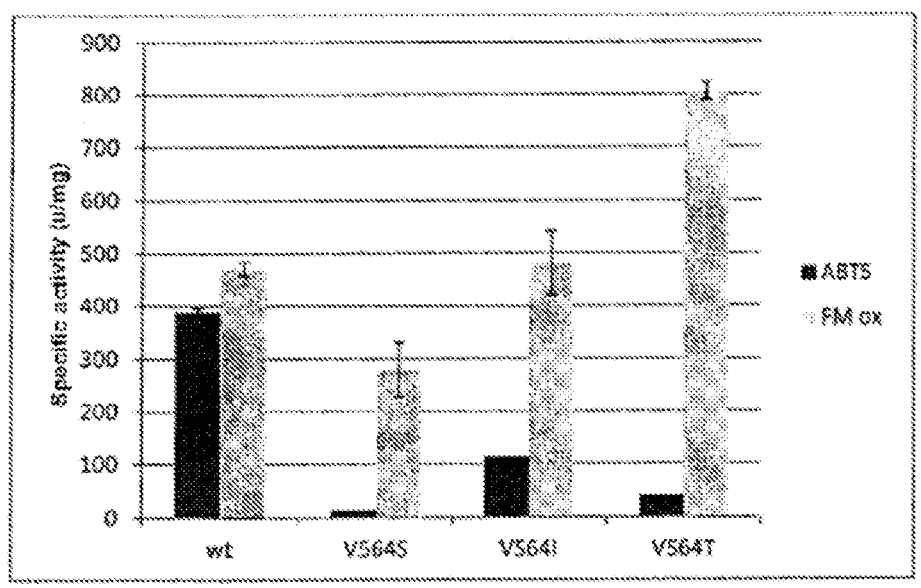
FIG. 3 is a graph illustrating the specific activity in U/mg of wild-type and mutant GOx from *Penicillium amagasakiense*.

The tests are performed in a 50 mM pH 7.5 phosphate buffer at 37° C. in a volume of 3 ml containing 1 mM of FMox and 150 mM glucose. The ferrocenemethanol reduction is monitored at 625 nm as a function of time (ε=0.413 mM$^{-1}$·cm$^{-1}$) The specific activity of the enzyme is expressed in micromoles of product appeared per mg of enzyme (U/mg) (FIG. 3). The enzyme is diluted to 50 nM so as to be able to measure a slope of between 0.001 and 0.1 OD$_{625\,nm}$/min.

It is noted that the four mutants show a marked decrease in activity toward oxygen relative to the wild-type GOx.

The activity toward ferrocenemethanol is different depending on the mutant. Thus, the V564S mutant has a lower activity, the V564I mutant has a similar activity, whereas the V564T mutant shows a strong increase in activity relative to the wild-type GOx.

Figure 4:
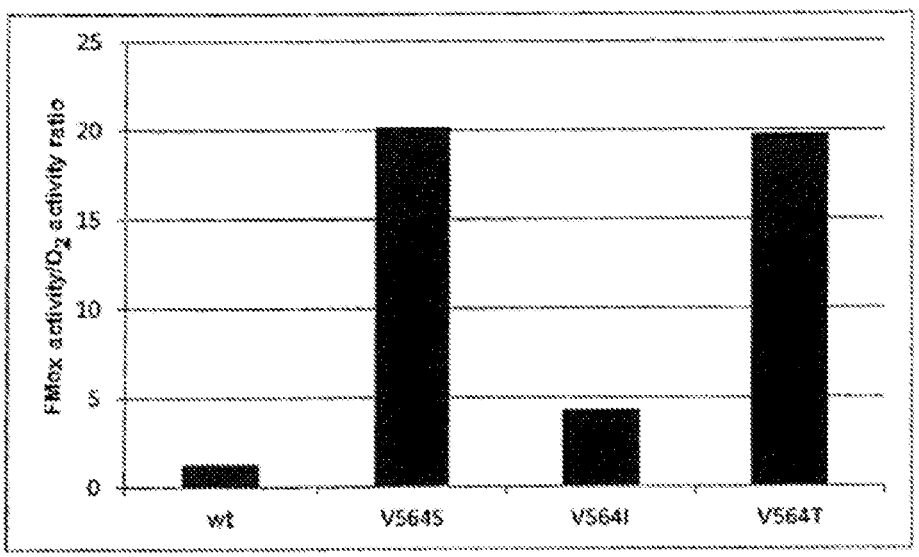
FIG. 4 is a graph representing the ferrocenemethanol activity/oxygen activity ratio.

The FMox activity/ABTS activity ratio makes it possible to obtain the specificity of the enzyme toward the substrate (ABTS or FMox). The greater the ratio, the less sensitive the enzyme is to oxygen (FIG. 4).

It is noted that the mutants V564S and V564T are very insensitive to oxygen, which makes them good candidates for use in electrochemical systems.

Figure 5:
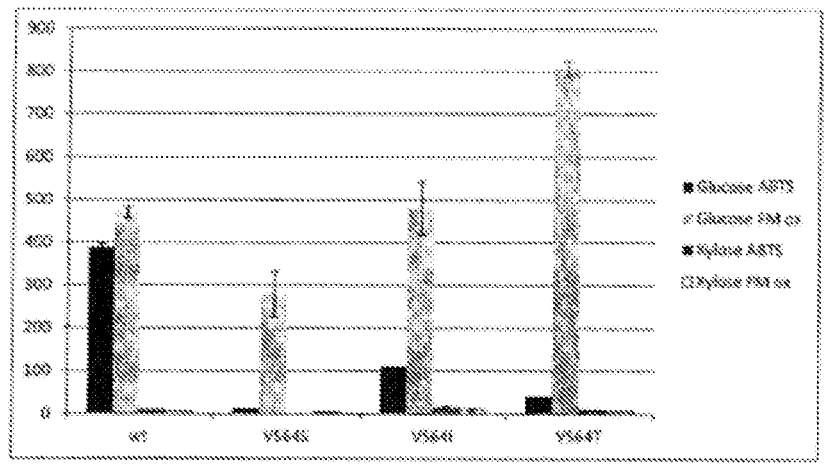
FIG. 5 shows a comparison of the specific activity of the wild-type and mutant GOx with glucose and xylose.

The same enzymatic tests were performed in the presence of xylose (FIG. 5): the ABTS and FMox activities for xylose are very low compared with the activities for glucose. Xylose does not come into competition with glucose as a substrate for the wild-type and mutant glucose oxidases of *Penicillium amagasakiense*.

5. Electrochemical Tests

Figure 6:
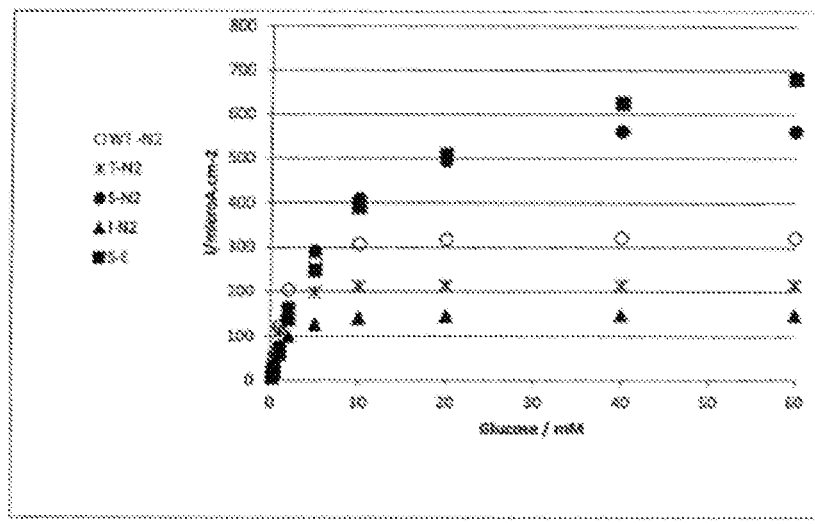
FIG. 6 is a graph representing the change in glucose oxidation current as a function of the glucose concentration.
Figure 7:
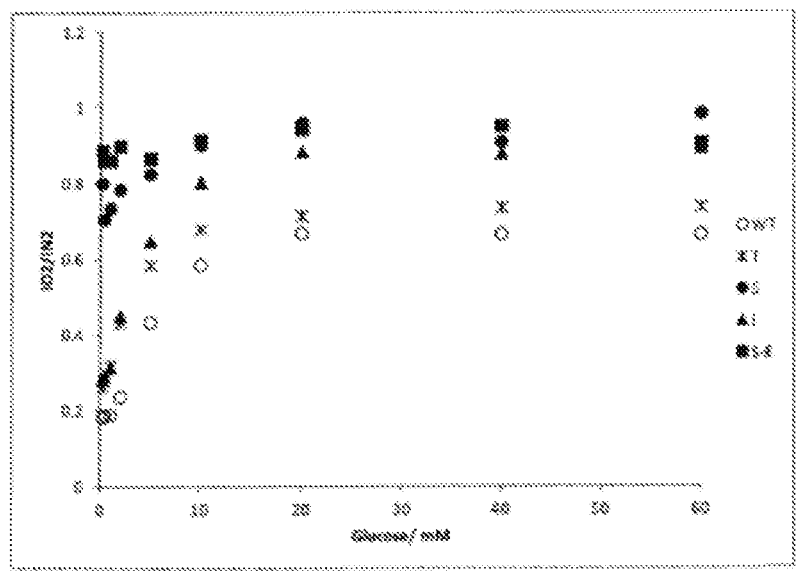
FIG. 7 is a graph representing the change in the ratio of the glucose oxidation current under oxygen divided by the current under argon as a function of the glucose concentration.

By way of example, FIG. 6 represents the change in the glucose oxidation current as a function of the glucose concentration in a PBS buffer under argon and at 37° C. Each electrode is composed of 5% by mass of glucose oxidase, 10% by mass of crosslinking agent and 75% by mass of redox polymer. FIG. 7 represents the change in the ratio of the glucose oxidation current under oxygen divided by the current under argon as a function of the glucose concentration. This figure clearly shows a decrease in the effect of oxygen on the glucose oxidation when the mutated enzymes are used.

The invention claimed is:

1. A glucose oxidase ($GO_x$) mutant with a percentage of identity of at least 95%, relative to the wild-type GOx of *Penicillium amagasakiense*, characterized in that its amino acid in position 564, with reference to the protein sequence of the wild-type GOx of *Penicillium amagasakiense* of SEQ. ID. No. 2, is replaced with an amino acid selected from the group consisting of a serine (V564S mutant), a threonine (V564T mutant) or an isoleucine (V564I mutant).

2. The GOx mutant as claimed in claim 1, characterized in that the V564S mutant also comprises a replacement of the lysine in position 424 with a glutamic acid (V564S+K424E mutant), glutamine (V564S+K424Q mutant), methionine (V564S+K424M mutant) or leucine (V564S+K424L mutant).

3. The GOx mutant as claimed in claim 1, characterized in that it has an amino acid sequence selected from the group consisting of SEQ. ID. No. 4, 6, 8, 10, 22, 24 and 26.

4. An isolated nucleic acid molecule, characterized in that it codes for a GOx mutant as claimed in claim 1.

5. The nucleic acid molecule as claimed in claim 4, characterized in that it is obtained by mutation of the nucleic acid molecule of sequence SEQ. ID. No. 1 with an oligonucleotide pair selected from the group consisting of pairs of SEQ. ID. No. 13 and 14; 15 and 16; 17 and 18; 19 and 20; 27 and 28; 29 and 30 and 31 and 32.

6. The nucleic acid molecule as claimed in claim 4, characterized in that it has a sequence selected from the group consisting of SEQ. ID. No. 3, 5, 7, 9, 21, 23 and 25.

7. An expression vector, characterized in that it comprises a nucleic acid molecule as claimed in claim 4.

8. An isolated host cell expressing an enzyme, characterized in that it is transformed with an expression vector as claimed in claim 7.

9. The method of use of a GOx mutant as claimed in claim 1, for measuring the glucose concentration in a sample.

10. The method as claimed in claim 9, characterized in that the sample is a biological sample, and in particular is blood.

11. A glucose assay kit, characterized in that it comprises a GOx mutant as claimed in claim 1.

12. A glucose electrode, characterized in that it comprises a conductive material covered with a deposit comprising at least one GOx mutant as claimed in claim 1.

13. A glucose sensor, characterized in that it consists of an electrode as claimed in claim 12.

14. A glucose biocell, characterized in that it comprises a first electrode as claimed in claim 12 as anode and a second electrode as cathode.

15. A process for assaying in solution glucose of a sample, characterized in that it comprises the following steps:
   a) introduction into said sample of a redox reagent whose reduction leads to a color change and of a GOx mutant as claimed in claim 1;
   b) measurement of the coloration intensity of the sample after enzymatic reaction;
   c) comparison of the coloration intensity measured in step b) with the intensity measured for standard solutions having a known glucose content;
   d) determination of the glucose concentration of said sample.

16. A process for assaying the glucose of a sample, characterized in that it comprises the following steps:
   a) introduction into said sample of a glucose electrode as claimed in claim 12;
   b) measurement of the intensity of the current in the sample;
   c) comparison of the intensity of the current measured in step b) with the intensity measured for standard solutions having a known glucose content;
   d) determination of the glucose concentration of said sample.

* * * * *

SEQUENCE LISTING

```
<160> NUMBER OF SEQ ID NOS: 32

<210> SEQ ID NO 1
<211> LENGTH: 7001
<212> TYPE: DNA
<213> ORGANISM: Penicillium amagasakiense

<400> SEQUENCE: 1
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120 cttctcgcc acgttcgccg gctttccccg tcaagctcta aatcgggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta taagggattt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttattttc taaatacatt caaatatgta     540
tccgctcatg aattaattct tagaaaaact catcgagcat caaatgaaac tgcaatttat     600
tcatatcagg attatcaata ccatatttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga gacgaaatac gcgatcgctg ttaaaaggac     960
aattacaaac aggaatcgaa tgcaaccggc gcaggaacac tgccagcgca tcaacaatat    1020
```

-continued

```
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200 cttttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
```

```
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg cgcgcattg    3840 cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920 gcgcggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgtacctg cctgcccaac agattgatgt    5100
ccagtctagt cttctcagtg accctagcaa ggttgcagga aagacctatg attacatcat    5160
tgctggtggt ggtttgactg gccttactgt tgctgccaaa ttgacagaaa accccaagat    5220
caaagtcctg gtcattgaaa agggcttcta tgagtccaac gatggagcca tcatcgagga    5280
tccaaatgct tatggacaaa tctttggcac cactgttgac cagaactacc tcaccgttcc    5340
cctgatcaac aaccgcacga acaatatcaa ggccggtaaa ggtcttggag atcaaccttt    5400
gataaacggt gactcctgga ctcgcccaga caaagtccag attgattctt gggagaaggt    5460 cttggcatg gaaggttgga attgggacaa catgttcgag tacatgaaga aggccgaggc    5520
tgcacgtacc cctactgctg ctcagcttgc tgctggccac tccttcaatg ctacctgcca    5580
tggaaccaac ggtactgttc aatccggagc ccgtgacaac ggccagcctt ggtctcctat    5640
tatgaaggcc cttatgaaca ccgtctcggc ccttggtgtc cccgtacagc aagactttct    5700
ctgtggtcat ccacgaggtg tctctatgat catgaacaat ctcgacgaaa accaagttcg    5760
```

-continued

```
tgttgatgct gcccgtgcat ggctgcttcc caactaccag cgctcgaatt tggagatcct   5820
tactggtcag atggttggaa aggttctgtt taaacagacc gcatccggtc cccaggctgt   5880
tggtgtgaac ttcggtacta ataaggccgt caactttgac gtctttgcta agcatgaggt   5940
ccttttggct gctggctcag ctatctctcc gctgatcttg gaatattctg cataggctt    6000
gaagtctgtt cttgatcaag ccaatgtcac tcagcttctt gatcttcctg ttggtatcaa   6060
tatgcaagat cagaccacaa ccactgtcag ttcccgtgct agttccgctg gtgctggtca   6120
gggtcaggcc gtcttcttcg ccaatttcac tgagaccttc ggtgactacg ccccccaggc   6180
cagggactta ctcaacacca agctcgacca atgggccgag agaccgttg cgcgcggtgg    6240
tttccataat gtaactgctc tcaaagtaca atacgaaaac tatcgtaact ggctccttga   6300
cgaagacgtc gccttcgccg agcttttcat ggacaccgag ggcaagatca acttcgattt   6360
atgggatctc atccctttca ctcgtggttc cgtccatatc ctcagtagcg atccttacct   6420
atggcaattc gccaacgacc ccaaattctt cctgaacgag tttgacctcc ttggtcaagc   6480
tgccgcttcc aagcttgctc gtgatctcac tagccaaggc gctatgaagg agtacttcgc   6540
cggggagact cttccaggat acaacttggt ccagaatgct actctttccc agtggtcgga   6600
ttatgtctta cagaacttcc gtcccaactg gcatgctgtg agcagctgct ctatgatgtc   6660
tagagagctt ggtggtgtcg ttgatgctac tgccaaggtg tacggtaccc aaggcctacg   6720
tgtcattgac gggtctattc ctccgactca ggtgtcttcc catgtcatga ccatttccta   6780
cggaatggct ttgaaggttg ctgatgccat tttggatgac tatgccaaaa gtgcctcgct   6840
cgagcaccac caccaccacc actgagatcc ggctgctaac aaagcccgaa aggaagctga   6900
gttggctgct gccaccgctg agcaataact agcataaccc cttggggcct ctaaacgggt   6960
cttgaggggt tttttgctga aaggaggaac tatatccgga t                      7001
```

<210> SEQ ID NO 2
<211> LENGTH: 587
<212> TYPE: PRT
<213> ORGANISM: Penicillium amagasakiense

<400> SEQUENCE: 2

```
Tyr Leu Pro Ala Gln Gln Ile Asp Val Gln Ser Ser Leu Leu Ser Asp
1               5                   10                  15

Pro Ser Lys Val Ala Gly Lys Thr Tyr Asp Tyr Ile Ile Ala Gly Gly
            20                  25                  30

Gly Leu Thr Gly Leu Thr Val Ala Ala Lys Leu Thr Glu Asn Pro Lys
        35                  40                  45

Ile Lys Val Leu Val Ile Glu Lys Gly Phe Tyr Glu Ser Asn Asp Gly
    50                  55                  60

Ala Ile Ile Glu Asp Pro Asn Ala Tyr Gly Gln Ile Phe Gly Thr Thr
65                  70                  75                  80

Val Asp Gln Asn Tyr Leu Thr Val Pro Leu Ile Asn Asn Pro Thr Asn
                85                  90                  95

Asn Ile Lys Ala Gly Lys Gly Leu Gly Gly Ser Thr Leu Ile Asn Gly
            100                 105                 110

Asp Ser Trp Thr Arg Pro Asp Lys Val Gln Ile Asp Ser Trp Glu Lys
        115                 120                 125

Val Phe Gly Met Glu Gly Trp Asn Trp Asp Asn Met Phe Glu Tyr Met
    130                 135                 140

Lys Lys Ala Glu Ala Ala Arg Thr Pro Thr Ala Ala Gln Leu Ala Ala
```

-continued

```
            145                 150                 155                 160
        Gly His Ser Phe Asn Pro Thr Cys His Gly Thr Asn Pro Thr Val Gln
                            165                 170                 175
        Ser Gly Ala Arg Asp Asn Gly Gln Pro Trp Ser Pro Ile Met Lys Ala
                            180                 185                 190
        Leu Met Asn Thr Val Ser Ala Leu Gly Val Pro Val Gln Gln Asp Phe
                            195                 200                 205
        Leu Cys Gly His Pro Arg Gly Val Ser Met Ile Met Asn Asn Leu Asp
                            210                 215                 220
        Glu Asn Gln Val Arg Val Asp Ala Ala Arg Ala Trp Leu Leu Pro Asn
        225                 230                 235                 240
        Tyr Gln Arg Ser Asn Leu Glu Ile Leu Thr Gly Gln Met Val Gly Lys
                            245                 250                 255
        Val Leu Phe Lys Gln Thr Ala Ser Gly Pro Gln Ala Val Gly Val Asn
                            260                 265                 270
        Phe Gly Thr Asn Lys Ala Val Asn Phe Asp Val Phe Ala Lys His Glu
                            275                 280                 285
        Val Leu Leu Ala Ala Gly Ser Ala Ile Ser Pro Leu Ile Leu Glu Tyr
                            290                 295                 300
        Ser Gly Ile Gly Leu Lys Ser Val Leu Asp Gln Ala Asn Pro Thr Gln
        305                 310                 315                 320
        Leu Leu Asp Leu Pro Val Gly Ile Asn Met Gln Asp Gln Thr Thr Thr
                            325                 330                 335
        Thr Val Ser Ser Arg Ala Ser Ser Ala Gly Ala Gly Gln Gly Gln Ala
                            340                 345                 350
        Val Phe Phe Ala Asn Pro Thr Glu Thr Phe Gly Asp Tyr Ala Pro Gln
                            355                 360                 365
        Ala Arg Asp Leu Leu Asn Thr Lys Leu Asp Gln Trp Ala Glu Glu Thr
                            370                 375                 380
        Val Ala Arg Gly Gly Phe His Asn Pro Thr Ala Leu Lys Val Gln Tyr
        385                 390                 395                 400
        Glu Asn Tyr Arg Asn Trp Leu Leu Asp Glu Asp Val Ala Phe Ala Glu
                            405                 410                 415
        Leu Phe Met Asp Thr Glu Gly Lys Ile Asn Phe Asp Leu Trp Asp Leu
                            420                 425                 430
        Ile Pro Phe Thr Arg Gly Ser Val His Ile Leu Ser Ser Asp Pro Tyr
                            435                 440                 445
        Leu Trp Gln Phe Ala Asn Asp Pro Lys Phe Phe Leu Asn Glu Phe Asp
                            450                 455                 460
        Leu Leu Gly Gln Ala Ala Ala Ser Lys Leu Ala Arg Asp Leu Thr Ser
        465                 470                 475                 480
        Gln Gly Ala Met Lys Glu Tyr Phe Ala Gly Glu Thr Leu Pro Gly Tyr
                            485                 490                 495
        Asn Leu Val Gln Asn Pro Thr Leu Ser Gln Trp Ser Asp Tyr Val Leu
                            500                 505                 510
        Gln Asn Phe Arg Pro Asn Trp His Ala Val Ser Ser Cys Ser Met Met
                            515                 520                 525
        Ser Arg Glu Leu Gly Gly Val Asp Ala Thr Ala Lys Val Tyr Gly
                            530                 535                 540
        Thr Gln Gly Leu Arg Val Ile Asp Gly Ser Ile Pro Pro Thr Gln Val
        545                 550                 555                 560
        Ser Ser His Val Met Thr Ile Phe Tyr Gly Met Ala Leu Lys Val Ala
                            565                 570                 575
```

Asp Ala Ile Leu Asp Asp Tyr Ala Lys Ser Ala
            580                 585

<210> SEQ ID NO 3
<211> LENGTH: 1770
<212> TYPE: DNA
<213> ORGANISM: Penicillium amagasakiense

<400> SEQUENCE: 3

| | | | |
|---|---|---|---|
| tatgtacctg cctgcccaac agattgatgt ccagtctagt cttctcagtg accctagcaa | 60 |
| ggttgcagga aagacctatg attacatcat tgctggtggt ggtttgactg gccttactgt | 120 |
| tgctgccaaa ttgacagaaa accccaagat caaagtcctg gtcattgaaa agggcttcta | 180 |
| tgagtccaac gatggagcca tcatcgagga tccaaatgct tatggacaaa tctttggcac | 240 |
| cactgttgac cagaactacc tcaccgttcc cctgatcaac aaccgcacga acaatatcaa | 300 |
| ggccggtaaa ggtcttggag atcaacctt gataaacggt gactcctgga ctcgcccaga | 360 |
| caaagtccag attgattctt gggagaaggt ctttggcatg aaggttgga attgggacaa | 420 |
| catgttcgag tacatgaaga aggccgaggc tgcacgtacc cctactgctg ctcagcttgc | 480 |
| tgctggccac tccttcaatg ctacctgcca tggaaccaac ggtactgttc aatccggagc | 540 |
| ccgtgacaac ggccagcctt ggtctcctat tatgaaggcc cttatgaaca ccgtctcggc | 600 |
| ccttggtgtc cccgtacagc aagactttct ctgtggtcat ccacgaggtg tctctatgat | 660 |
| catgaacaat ctcgacgaaa accaagttcg tgttgatgct gcccgtgcat ggctgcttcc | 720 |
| caactaccag cgctcgaatt tggagatcct tactggtcag atggttggaa aggttctgtt | 780 |
| taaacagacc gcatccggtc cccaggctgt tggtgtgaac ttcggtacta ataaggccgt | 840 |
| caactttgac gtctttgcta agcatgaggt ccttttggct gctggctcag ctatctctcc | 900 |
| gctgatcttg gaatattctg gcataggctt gaagtctgtt cttgatcaag ccaatgtcac | 960 |
| tcagcttctt gatcttcctg ttggtatcaa tatgcaagat cagaccacaa ccactgtcag | 1020 |
| ttcccgtgct agttccgctg tgctggtca gggtcaggcc gtcttcttcg ccaatttcac | 1080 |
| tgagaccttc ggtgactacg cccccccaggc cagggactta tcaacacca agctcgacca | 1140 |
| atgggccgag gagaccgttg cgcgcggtgg tttccataat gtaactgctc tcaaagtaca | 1200 |
| atacgaaaac tatcgtaact ggctccttga cgaagacgtc gccttcgccg agcttttcat | 1260 |
| ggacaccgag ggcaagatca acttcgattt atgggatctc atccctttca ctcgtggttc | 1320 |
| cgtccatatc ctcagtagcg atccttacct atggcaattc gccaacgacc caaattctt | 1380 |
| cctgaacgag tttgacctcc ttggtcaagc tgccgcttcc aagcttgctc gtgatctcac | 1440 |
| tagccaaggc gctatgaagg agtacttcgc cggggagact cttccaggat acaacttggt | 1500 |
| ccagaatgct actcttctccc agtggtcgga ttatgtctta cagaacttcc gtcccaactg | 1560 |
| gcatgctgtg agcagctgct ctatgatgtc tagagagctt ggtggtgtcg ttgatgctac | 1620 |
| tgccaaggtg tacggtaccc aaggcctacg tgtcattgac gggtctattc ctccgactca | 1680 |
| ggtgtcttcc cattccatga ccattttcta cggaatggct ttgaaggttg ctgatgccat | 1740 |
| tttggatgac tatgccaaaa gtgcctcgct | 1770 |

<210> SEQ ID NO 4
<211> LENGTH: 587
<212> TYPE: PRT
<213> ORGANISM: Penicillium amagasakiense

<400> SEQUENCE: 4

```
Tyr Leu Pro Ala Gln Ile Asp Val Gln Ser Ser Leu Leu Ser Asp
1               5                   10                  15

Pro Ser Lys Val Ala Gly Lys Thr Tyr Asp Tyr Ile Ile Ala Gly Gly
            20                  25                  30

Gly Leu Thr Gly Leu Thr Val Ala Ala Lys Leu Thr Glu Asn Pro Lys
                35                  40                  45

Ile Lys Val Leu Val Ile Glu Lys Gly Phe Tyr Glu Ser Asn Asp Gly
        50                  55                  60

Ala Ile Ile Glu Asp Pro Asn Ala Tyr Gly Gln Ile Phe Gly Thr Thr
65                  70                  75                  80

Val Asp Gln Asn Tyr Leu Thr Val Pro Leu Ile Asn Asn Pro Thr Asn
                85                  90                  95

Asn Ile Lys Ala Gly Lys Gly Leu Gly Gly Ser Thr Leu Ile Asn Gly
                100                 105                 110

Asp Ser Trp Thr Arg Pro Asp Lys Val Gln Ile Asp Ser Trp Glu Lys
            115                 120                 125

Val Phe Gly Met Glu Gly Trp Asn Trp Asp Asn Met Phe Glu Tyr Met
130                 135                 140

Lys Lys Ala Glu Ala Ala Arg Thr Pro Thr Ala Ala Gln Leu Ala Ala
145                 150                 155                 160

Gly His Ser Phe Asn Pro Thr Cys His Gly Thr Asn Pro Thr Val Gln
                165                 170                 175

Ser Gly Ala Arg Asp Asn Gly Gln Pro Trp Ser Pro Ile Met Lys Ala
            180                 185                 190

Leu Met Asn Thr Val Ser Ala Leu Gly Val Pro Val Gln Gln Asp Phe
        195                 200                 205

Leu Cys Gly His Pro Arg Gly Val Ser Met Ile Met Asn Asn Leu Asp
    210                 215                 220

Glu Asn Gln Val Arg Val Asp Ala Ala Arg Ala Trp Leu Leu Pro Asn
225                 230                 235                 240

Tyr Gln Arg Ser Asn Leu Glu Ile Leu Thr Gly Gln Met Val Gly Lys
                245                 250                 255

Val Leu Phe Lys Gln Thr Ala Ser Gly Pro Gln Ala Val Gly Val Asn
            260                 265                 270

Phe Gly Thr Asn Lys Ala Val Asn Phe Asp Val Phe Ala Lys His Glu
        275                 280                 285

Val Leu Leu Ala Ala Gly Ser Ala Ile Ser Pro Leu Ile Leu Glu Tyr
    290                 295                 300

Ser Gly Ile Gly Leu Lys Ser Val Leu Asp Gln Ala Asn Pro Thr Gln
305                 310                 315                 320

Leu Leu Asp Leu Pro Val Gly Ile Asn Met Gln Asp Gln Thr Thr Thr
                325                 330                 335

Thr Val Ser Ser Arg Ala Ser Ser Ala Gly Ala Gly Gln Gly Gln Ala
            340                 345                 350

Val Phe Phe Ala Asn Pro Thr Glu Thr Phe Gly Asp Tyr Ala Pro Gln
        355                 360                 365

Ala Arg Asp Leu Leu Asn Thr Lys Leu Asp Gln Trp Ala Glu Glu Thr
    370                 375                 380

Val Ala Arg Gly Gly Phe His Asn Pro Thr Ala Leu Lys Val Gln Tyr
385                 390                 395                 400

Glu Asn Tyr Arg Asn Trp Leu Leu Asp Glu Asp Val Ala Phe Ala Glu
                405                 410                 415
```

Leu Phe Met Asp Thr Glu Gly Lys Ile Asn Phe Asp Leu Trp Asp Leu
                420                 425                 430

Ile Pro Phe Thr Arg Gly Ser Val His Ile Leu Ser Ser Asp Pro Tyr
        435                 440                 445

Leu Trp Gln Phe Ala Asn Asp Pro Lys Phe Leu Asn Glu Phe Asp
    450                 455                 460

Leu Leu Gly Gln Ala Ala Ser Lys Leu Ala Arg Asp Leu Thr Ser
465                 470                 475                 480

Gln Gly Ala Met Lys Glu Tyr Phe Ala Gly Thr Leu Pro Gly Tyr
                485                 490                 495

Asn Leu Val Gln Asn Pro Thr Leu Ser Gln Trp Ser Asp Tyr Val Leu
                500                 505                 510

Gln Asn Phe Arg Pro Asn Trp His Ala Val Ser Ser Cys Ser Met Met
            515                 520                 525

Ser Arg Glu Leu Gly Gly Val Val Asp Ala Thr Ala Lys Val Tyr Gly
            530                 535                 540

Thr Gln Gly Leu Arg Val Ile Asp Gly Ser Ile Pro Pro Thr Gln Val
545                 550                 555                 560

Ser Ser His Ser Met Thr Ile Phe Tyr Gly Met Ala Leu Lys Val Ala
                565                 570                 575

Asp Ala Ile Leu Asp Asp Tyr Ala Lys Ser Ala
            580                 585

<210> SEQ ID NO 5
<211> LENGTH: 1768
<212> TYPE: DNA
<213> ORGANISM: Penicillium amagasakiense

<400> SEQUENCE: 5

| | | |
|---|---|---|
| tatgtacctg cctgcccaac agattgatgt ccagtctagt cttctcagtg accctagcaa | 60 |
| ggttgcagga aagacctatg attacatcat tgctggtggt ggtttgactg gccttactgt | 120 |
| tgctgccaaa ttgacagaaa accccaagat caaagtcctg gtcattgaaa agggcttcta | 180 |
| tgagtccaac gatggagcca tcatcgagga tccaaatgct tatggacaaa tctttggcac | 240 |
| cactgttgac cagaactacc tcaccgttcc cctgatcaac aaccgcacga caatatcaa | 300 |
| ggccggtaaa ggtcttggag atcaaccttg ataaacggtg actcctggac tcgcccagac | 360 |
| aaagtccaga ttgattcttg ggagaaggtc tttggcatga aggttggaat gggacaaca | 420 |
| tgttcgagta catgaagaag gccgaggctg cacgtacccc tactgctgct cagcttgctg | 480 |
| ctggccactc cttcaatgct acctgccatg aaccaacgg tactgttcaa tccggagccc | 540 |
| gtgacaacgg ccagccttgg tctcctatta tgaaggccct tatgaacacc gtctcggccc | 600 |
| ttggtgtccc cgtacagcaa gactttctct gtggtcatcc acgaggtgtc tctatgatca | 660 |
| tgaacaatct cgacgaaaac caagttcgtg ttgatgctgc ccgtgcatgg ctgcttccca | 720 |
| actaccagcg ctcgaatttg gagatcctta ctggtcagat ggttggaaag gttctgttta | 780 |
| aacagaccgc atccggtccc caggctgttg gtgtgaactt cggtactaat aaggccgtca | 840 |
| actttgacgt ctttgctaag catgaggtcc ttttggctgc tggctcagct atctctccgc | 900 |
| tgatcttgga atattctggc ataggcttga agtctgttct tgatcaagcc aatgtcactc | 960 |
| agcttcttga tcttcctgtt ggtatcaata tgcaagatca gaccacaacc actgtcagtt | 1020 |
| cccgtgctag ttccgctggt gctggtcagg tcaggccgt cttcttcgcc aatttcactg | 1080 |
| agaccttcgg tgactacgcc ccccaggcca gggacttact caacaccaag ctcgaccaat | 1140 |

-continued

```
gggccgagga gaccgttgcg cgcggtggtt tccataatgt aactgctctc aaagtacaat    1200
acgaaaacta tcgtaactgg ctccttgacg aagacgtcgc cttcgccgag cttttcatgg    1260
acaccgaggg caagatcaac ttcgatttat gggatctcat ccctttcact cgtggttccg    1320
tccatatcct cagtagcgat ccttacctat ggcaattcgc caacgacccc aaattcttcc    1380
tgaacgagtt tgacctcctt ggtcaagctg ccgcttccaa gcttgctcgt gatctcacta    1440
gccaaggcgc tatgaaggag tacttcgccg gggagactct tccaggatac aacttggtcc    1500
agaatgctac tctttcccag tggtcggatt atgtcttaca gaacttccgt cccaactggc    1560
atgctgtgag cagctgctct atgatgtcta gagagcttgg tggtgtcgtt gatgctactg    1620
ccaaggtgta cggtacccaa ggcctacgtg tcattgacgg gtctattcct ccgactcagg    1680
tgtcttccca taccatgacc attttctacg gaatggcttt gaaggttgct gatgccattt    1740
tggatgacta tgccaaaagt gcctcgct                                        1768
```

<210> SEQ ID NO 6
<211> LENGTH: 587
<212> TYPE: PRT
<213> ORGANISM: Penicillium amagasakiense

<400> SEQUENCE: 6

```
Tyr Leu Pro Ala Gln Gln Ile Asp Val Gln Ser Ser Leu Leu Ser Asp
1               5                   10                  15

Pro Ser Lys Val Ala Gly Lys Thr Tyr Asp Tyr Ile Ile Ala Gly Gly
                20                  25                  30

Gly Leu Thr Gly Leu Thr Val Ala Ala Lys Leu Thr Glu Asn Pro Lys
            35                  40                  45

Ile Lys Val Leu Val Ile Glu Lys Gly Phe Tyr Glu Ser Asn Asp Gly
        50                  55                  60

Ala Ile Ile Glu Asp Pro Asn Ala Tyr Gly Gln Ile Phe Gly Thr Thr
65                  70                  75                  80

Val Asp Gln Asn Tyr Leu Thr Val Pro Leu Ile Asn Asn Pro Thr Asn
                85                  90                  95

Asn Ile Lys Ala Gly Lys Gly Leu Gly Gly Ser Thr Leu Ile Asn Gly
                100                 105                 110

Asp Ser Trp Thr Arg Pro Asp Lys Val Gln Ile Asp Ser Trp Glu Lys
            115                 120                 125

Val Phe Gly Met Glu Gly Trp Asn Trp Asp Asn Met Phe Glu Tyr Met
        130                 135                 140

Lys Lys Ala Glu Ala Ala Arg Thr Pro Thr Ala Ala Gln Leu Ala Ala
145                 150                 155                 160

Gly His Ser Phe Asn Pro Thr Cys His Gly Thr Asn Pro Thr Val Gln
                165                 170                 175

Ser Gly Ala Arg Asp Asn Gly Gln Pro Trp Ser Pro Ile Met Lys Ala
            180                 185                 190

Leu Met Asn Thr Val Ser Ala Leu Gly Val Pro Val Gln Gln Asp Phe
        195                 200                 205

Leu Cys Gly His Pro Arg Gly Val Ser Met Ile Met Asn Asn Leu Asp
    210                 215                 220

Glu Asn Gln Val Arg Val Asp Ala Ala Arg Ala Trp Leu Leu Pro Asn
225                 230                 235                 240

Tyr Gln Arg Ser Asn Leu Glu Ile Leu Thr Gly Gln Met Val Gly Lys
                245                 250                 255

Val Leu Phe Lys Gln Thr Ala Ser Gly Pro Gln Ala Val Gly Val Asn
```

```
            260                 265                 270
Phe Gly Thr Asn Lys Ala Val Asn Phe Asp Val Phe Ala Lys His Glu
            275                 280                 285
Val Leu Leu Ala Ala Gly Ser Ala Ile Ser Pro Leu Ile Leu Glu Tyr
            290                 295                 300
Ser Gly Ile Gly Leu Lys Ser Val Leu Asp Gln Ala Asn Pro Thr Gln
305                 310                 315                 320
Leu Leu Asp Leu Pro Val Gly Ile Asn Met Gln Asp Gln Thr Thr Thr
                    325                 330                 335
Thr Val Ser Ser Arg Ala Ser Ser Ala Gly Ala Gly Gln Gly Gln Ala
                340                 345                 350
Val Phe Phe Ala Asn Pro Thr Glu Thr Phe Gly Asp Tyr Ala Pro Gln
            355                 360                 365
Ala Arg Asp Leu Leu Asn Thr Lys Leu Asp Gln Trp Ala Glu Glu Thr
            370                 375                 380
Val Ala Arg Gly Gly Phe His Asn Pro Thr Ala Leu Lys Val Gln Tyr
385                 390                 395                 400
Glu Asn Tyr Arg Asn Trp Leu Leu Asp Glu Asp Val Ala Phe Ala Glu
                    405                 410                 415
Leu Phe Met Asp Thr Glu Gly Lys Ile Asn Phe Asp Leu Trp Asp Leu
                420                 425                 430
Ile Pro Phe Thr Arg Gly Ser Val His Ile Leu Ser Ser Asp Pro Tyr
            435                 440                 445
Leu Trp Gln Phe Ala Asn Asp Pro Lys Phe Phe Leu Asn Glu Phe Asp
            450                 455                 460
Leu Leu Gly Gln Ala Ala Ala Ser Lys Leu Ala Arg Asp Leu Thr Ser
465                 470                 475                 480
Gln Gly Ala Met Lys Glu Tyr Phe Ala Gly Glu Thr Leu Pro Gly Tyr
                    485                 490                 495
Asn Leu Val Gln Asn Pro Thr Leu Ser Gln Trp Ser Asp Tyr Val Leu
                500                 505                 510
Gln Asn Phe Arg Pro Asn Trp His Ala Val Ser Ser Cys Ser Met Met
            515                 520                 525
Ser Arg Glu Leu Gly Gly Val Val Asp Ala Thr Ala Lys Val Tyr Gly
            530                 535                 540
Thr Gln Gly Leu Arg Val Ile Asp Gly Ser Ile Pro Pro Thr Gln Val
545                 550                 555                 560
Ser Ser His Thr Met Thr Ile Phe Tyr Gly Met Ala Leu Lys Val Ala
                    565                 570                 575
Asp Ala Ile Leu Asp Asp Tyr Ala Lys Ser Ala
                580                 585

<210> SEQ ID NO 7
<211> LENGTH: 1770
<212> TYPE: DNA
<213> ORGANISM: Penicillium amagasakiense

<400> SEQUENCE: 7
tatgtacctg cctgcccaac agattgatgt ccagtctagt cttctcagtg accctagcaa      60
ggttgcagga aagacctatg attacatcat tgctggtggt ggtttgactg gccttactgt     120
tgctgccaaa ttgacagaaa accccaagat caaagtcctg gtcattgaaa agggcttcta     180
tgagtccaac gatggagcca tcatcgagga tccaaatgct tatggacaaa tctttggcac     240
cactgttgac cagaactacc tcaccgttcc cctgatcaac aaccgcacga acaatatcaa     300
```

```
ggccggtaaa ggtcttggag gatcaaccct gataaacggt gactcctgga ctcgcccaga    360
caaagtccag attgattctt gggagaaggt ctttggcatg gaaggttgga attgggacaa    420
catgttcgag tacatgaaga aggccgaggc tgcacgtacc cctactgctg ctcagcttgc    480
tgctggccac tccttcaatg ctacctgcca tggaaccaac ggtactgttc aatccggagc    540
ccgtgacaac ggccagcctt ggtctcctat tatgaaggcc cttatgaaca ccgtctcggc    600
ccttggtgtc cccgtacagc aagactttct ctgtggtcat ccacgaggtg tctctatgat    660
catgaacaat ctcgacgaaa accaagttcg tgttgatgct gcccgtgcat ggctgcttcc    720
caactaccag cgctcgaatt tggagatcct tactggtcag atggttggaa aggttctgtt    780
taaacagacc gcatccggtc cccaggctgt tggtgtgaac ttcggtacta ataaggccgt    840
caactttgac gtctttgcta agcatgaggt ccttttggct gctggctcag ctatctctcc    900
gctgatcttg gaatattctg gcataggctt gaagtctgtt cttgatcaag ccaatgtcac    960
tcagcttctt gatcttcctg ttggtatcaa tatgcaagat cagaccacaa ccactgtcag   1020
ttcccgtgct agttccgctg gtgctggtca gggtcaggcc gtcttcttcg ccaatttcac   1080
tgagaccttc ggtgactacg ccccccaggc cagggactta ctcaacacca agctcgacca   1140
atgggccgag gagaccgttg cgcgcggtgg tttccataat gtaactgctc tcaaagtaca   1200
atacgaaaac tatcgtaact ggctccttga cgaagacgtc gccttcgccg agcttttcat   1260
ggacaccgag ggcaagatca acttcgattt atgggatctc atccctttca ctcgtggttc   1320
cgtcccatat ctcagtagcg atccttacct atggcaattc gccaacgacc ccaaattctt   1380
cctgaacgag tttgacctcc ttggtcaagc tgccgcttcc aagcttgctc gtgatctcac   1440
tagccaaggc gctatgaagg agtacttcgc cggggagact cttccaggat acaacttggt   1500
ccagaatgct actctttccc agtggtcgga ttatgtctta cagaacttcc gtcccaactg   1560
gcatgctgtg agcagctgct ctatgatgtc tagagagctt ggtggtgtcg ttgatgctac   1620
tgccaaggtg tacggtaccc aaggcctacg tgtcattgac gggtctattc ctccgactca   1680
ggtgtcttcc catattatga ccattttcta cggaatggct ttgaaggttg ctgatgccat   1740
tttggatgac tatgccaaaa gtgcctcgct                                    1770
```

<210> SEQ ID NO 8
<211> LENGTH: 587
<212> TYPE: PRT
<213> ORGANISM: Penicillium amagasakiense

<400> SEQUENCE: 8

```
Tyr Leu Pro Ala Gln Gln Ile Asp Val Gln Ser Ser Leu Leu Ser Asp
1               5                   10                  15

Pro Ser Lys Val Ala Gly Lys Thr Tyr Asp Tyr Ile Ile Ala Gly Gly
            20                  25                  30

Gly Leu Thr Gly Leu Thr Val Ala Ala Lys Leu Thr Glu Asn Pro Lys
        35                  40                  45

Ile Lys Val Leu Val Ile Glu Lys Gly Phe Tyr Glu Ser Asn Asp Gly
    50                  55                  60

Ala Ile Ile Glu Asp Pro Asn Ala Tyr Gly Gln Ile Phe Gly Thr Thr
65                  70                  75                  80

Val Asp Gln Asn Tyr Leu Thr Val Pro Leu Ile Asn Asn Pro Thr Asn
                85                  90                  95

Asn Ile Lys Ala Gly Lys Gly Leu Gly Gly Ser Thr Leu Ile Asn Gly
            100                 105                 110
```

```
Asp Ser Trp Thr Arg Pro Asp Lys Val Gln Ile Asp Ser Trp Glu Lys
        115                 120                 125

Val Phe Gly Met Glu Gly Trp Asn Trp Asp Asn Met Phe Glu Tyr Met
130                 135                 140

Lys Lys Ala Glu Ala Ala Arg Thr Pro Thr Ala Ala Gln Leu Ala Ala
145                 150                 155                 160

Gly His Ser Phe Asn Pro Thr Cys His Gly Thr Asn Pro Thr Val Gln
                    165                 170                 175

Ser Gly Ala Arg Asp Asn Gly Gln Pro Trp Ser Pro Ile Met Lys Ala
                180                 185                 190

Leu Met Asn Thr Val Ser Ala Leu Gly Val Pro Val Gln Gln Asp Phe
                195                 200                 205

Leu Cys Gly His Pro Arg Gly Val Ser Met Ile Met Asn Asn Leu Asp
        210                 215                 220

Glu Asn Gln Val Arg Val Asp Ala Ala Arg Ala Trp Leu Leu Pro Asn
225                 230                 235                 240

Tyr Gln Arg Ser Asn Leu Glu Ile Leu Thr Gly Gln Met Val Gly Lys
                245                 250                 255

Val Leu Phe Lys Gln Thr Ala Ser Gly Pro Gln Ala Val Gly Val Asn
        260                 265                 270

Phe Gly Thr Asn Lys Ala Val Asn Phe Asp Val Phe Ala Lys His Glu
        275                 280                 285

Val Leu Leu Ala Ala Gly Ser Ala Ile Ser Pro Leu Ile Leu Glu Tyr
        290                 295                 300

Ser Gly Ile Gly Leu Lys Ser Val Leu Asp Gln Ala Asn Pro Thr Gln
305                 310                 315                 320

Leu Leu Asp Leu Pro Val Gly Ile Asn Met Gln Asp Gln Thr Thr Thr
                325                 330                 335

Thr Val Ser Ser Arg Ala Ser Ser Ala Gly Ala Gly Gln Gly Gln Ala
                340                 345                 350

Val Phe Phe Ala Asn Pro Thr Glu Thr Phe Gly Asp Tyr Ala Pro Gln
        355                 360                 365

Ala Arg Asp Leu Leu Asn Thr Lys Leu Asp Gln Trp Ala Glu Glu Thr
        370                 375                 380

Val Ala Arg Gly Gly Phe His Asn Pro Thr Ala Leu Lys Val Gln Tyr
385                 390                 395                 400

Glu Asn Tyr Arg Asn Trp Leu Leu Asp Glu Asp Val Ala Phe Ala Glu
                405                 410                 415

Leu Phe Met Asp Thr Glu Gly Lys Ile Asn Phe Asp Leu Trp Asp Leu
                420                 425                 430

Ile Pro Phe Thr Arg Gly Ser Val His Ile Leu Ser Ser Asp Pro Tyr
                435                 440                 445

Leu Trp Gln Phe Ala Asn Asp Pro Lys Phe Phe Leu Asn Glu Phe Asp
        450                 455                 460

Leu Leu Gly Gln Ala Ala Ala Ser Lys Leu Ala Arg Asp Leu Thr Ser
465                 470                 475                 480

Gln Gly Ala Met Lys Glu Tyr Phe Ala Gly Glu Thr Leu Pro Gly Tyr
                485                 490                 495

Asn Leu Val Gln Asn Pro Thr Leu Ser Gln Trp Ser Asp Tyr Val Leu
                500                 505                 510

Gln Asn Phe Arg Pro Asn Trp His Ala Val Ser Ser Cys Ser Met Met
        515                 520                 525
```

Ser Arg Glu Leu Gly Gly Val Val Asp Ala Thr Ala Lys Val Tyr Gly
            530                 535                 540

Thr Gln Gly Leu Arg Val Ile Asp Gly Ser Ile Pro Pro Thr Gln Val
545                 550                 555                 560

Ser Ser His Ile Met Thr Ile Phe Tyr Gly Met Ala Leu Lys Val Ala
                565                 570                 575

Asp Ala Ile Leu Asp Asp Tyr Ala Lys Ser Ala
            580                 585

<210> SEQ ID NO 9
<211> LENGTH: 1770
<212> TYPE: DNA
<213> ORGANISM: Penicillium amagasakiense

<400> SEQUENCE: 9

```
tatgtacctg cctgcccaac agattgatgt ccagtctagt cttctcagtg accctagcaa      60
ggttgcagga aagacctatg attacatcat tgctggtggt ggtttgactg gccttactgt     120
tgctgccaaa ttgacagaaa accccaagat caaagtcctg gtcattgaaa agggcttcta     180
tgagtccaac gatggagcca tcatcgagga tccaaatgct tatggacaaa tctttggcac     240
cactgttgac cagaactacc tcaccgttcc cctgatcaac aaccgcacga caatatcaa     300
ggccggtaaa ggtcttggag atcaaccttg ataaacggt gactcctgga ctcgcccaga     360
caaagtccag attgattctt gggagaaggt ctttggcatg aaggttgga attgggacaa     420
catgttcgag tacatgaaga aggccgaggc tgcacgtacc cctactgctg ctcagcttgc     480
tgctggccac tccttcaatg ctacctgcca tggaaccaac ggtactgttc aatccggagc     540
ccgtgacaac ggccagcctt ggtctcctat tatgaaggcc ttatgaaca ccgtctcggc     600
ccttggtgtc cccgtacagc aagactttct ctgtggtcat ccacgaggtg tctctatgat     660
catgaacaat ctcgacgaaa accaagttcg tgttgatgct gcccgtgcat ggctgcttcc     720
caactaccag cgctcgaatt tggagatcct tactggtcag atggttggaa aggttctgtt     780
taaacagacc gcatccggtc cccaggctgt tggtgtgaac ttcggtacta ataaggccgt     840
caactttgac gtcttttgcta agcatgaggt ccttttggct gctggctcag ctatctctcc     900
gctgatcttg gaatattctg gcataggctt gaagtctgtt cttgatcaag ccaatgtcac     960
tcagcttctt gatcttcctg ttggtatcaa tatgcaagat cagaccacaa ccactgtcag    1020
ttcccgtgct agttccgctg gtgctggtca gggtcaggcc gtcttcttcg ccaatttcac    1080
tgagaccttc ggtgactacg cccccaggc cagggactta tcaacacca agctcgacca    1140
atgggccgag gagaccgttg cgcgcggtgg tttccataat gtaactgctc tcaaagtaca    1200
atacgaaaac tatcgtaact ggctccttga cgaagacgtc gccttcgccg agcttttcat    1260
ggacaccgag ggcgagatca acttcgattt atgggatctc atccctttca ctcgtggttc    1320
cgtccatatc ctcagtagcg atccttacct atggcaattc gccaacgacc ccaaattctt    1380
cctgaacgag tttgacctcc ttggtcaagc tgccgcttcc aagcttgctc gtgatctcac    1440
tagccaaggc gctatgaagg agtacttcgc cggggagact cttccaggat acaacttggt    1500
ccagaatgct actctttccc agtggtcgga ttatgtctta cagaacttcc gtcccaactg    1560
gcatgctgtg agcagctgct ctatgatgtc tagagagctt ggtggtgtcg ttgatgctac    1620
tgccaaggtg tacggtaccc aaggcctacg tgtcattgac gggtctattc ctccgactca    1680
ggtgtcttcc cattccatga ccattttcta cggaatggct tgaaggttg ctgatgccat    1740
tttggatgac tatgccaaaa gtgcctcgct                                    1770
```

<210> SEQ ID NO 10
<211> LENGTH: 587
<212> TYPE: PRT
<213> ORGANISM: Penicillium amagasakiense

<400> SEQUENCE: 10

```
Tyr Leu Pro Ala Gln Ile Asp Val Gln Ser Ser Leu Leu Ser Asp
1               5                   10                  15

Pro Ser Lys Val Ala Gly Lys Thr Tyr Asp Tyr Ile Ile Ala Gly Gly
            20                  25                  30

Gly Leu Thr Gly Leu Thr Val Ala Ala Lys Leu Thr Glu Asn Pro Lys
            35                  40                  45

Ile Lys Val Leu Val Ile Glu Lys Gly Phe Tyr Glu Ser Asn Asp Gly
50                  55                  60

Ala Ile Ile Glu Asp Pro Asn Ala Tyr Gly Gln Ile Phe Gly Thr Thr
65                  70                  75                  80

Val Asp Gln Asn Tyr Leu Thr Val Pro Leu Ile Asn Asn Pro Thr Asn
                85                  90                  95

Asn Ile Lys Ala Gly Lys Gly Leu Gly Gly Ser Thr Leu Ile Asn Gly
            100                 105                 110

Asp Ser Trp Thr Arg Pro Asp Lys Val Gln Ile Asp Ser Trp Glu Lys
            115                 120                 125

Val Phe Gly Met Glu Gly Trp Asn Trp Asp Asn Met Phe Glu Tyr Met
130                 135                 140

Lys Lys Ala Glu Ala Ala Arg Thr Pro Thr Ala Ala Gln Leu Ala Ala
145                 150                 155                 160

Gly His Ser Phe Asn Pro Thr Cys His Gly Thr Asn Pro Thr Val Gln
                165                 170                 175

Ser Gly Ala Arg Asp Asn Gly Gln Pro Trp Ser Pro Ile Met Lys Ala
            180                 185                 190

Leu Met Asn Thr Val Ser Ala Leu Gly Val Pro Val Gln Gln Asp Phe
            195                 200                 205

Leu Cys Gly His Pro Arg Gly Val Ser Met Ile Met Asn Asn Leu Asp
210                 215                 220

Glu Asn Gln Val Arg Val Asp Ala Ala Arg Ala Trp Leu Leu Pro Asn
225                 230                 235                 240

Tyr Gln Arg Ser Asn Leu Glu Ile Leu Thr Gly Gln Met Val Gly Lys
                245                 250                 255

Val Leu Phe Lys Gln Thr Ala Ser Gly Pro Gln Ala Val Gly Val Asn
            260                 265                 270

Phe Gly Thr Asn Lys Ala Val Asn Phe Asp Val Phe Ala Lys His Glu
            275                 280                 285

Val Leu Leu Ala Ala Gly Ser Ala Ile Ser Pro Leu Ile Leu Glu Tyr
290                 295                 300

Ser Gly Ile Gly Leu Lys Ser Val Leu Asp Gln Ala Asn Pro Thr Gln
305                 310                 315                 320

Leu Leu Asp Leu Pro Val Gly Ile Asn Met Gln Asp Gln Thr Thr Thr
                325                 330                 335

Thr Val Ser Ser Arg Ala Ser Ser Ala Gly Ala Gly Gln Gly Gln Ala
            340                 345                 350

Val Phe Phe Ala Asn Pro Thr Glu Thr Phe Gly Asp Tyr Ala Pro Gln
            355                 360                 365

Ala Arg Asp Leu Leu Asn Thr Lys Leu Asp Gln Trp Ala Glu Glu Thr
```

```
                370                 375                 380
Val Ala Arg Gly Gly Phe His Asn Pro Thr Ala Leu Lys Val Gln Tyr
385                 390                 395                 400

Glu Asn Tyr Arg Asn Trp Leu Leu Asp Glu Asp Val Ala Phe Ala Glu
                405                 410                 415

Leu Phe Met Asp Thr Glu Gly Glu Ile Asn Phe Asp Leu Trp Asp Leu
            420                 425                 430

Ile Pro Phe Thr Arg Gly Ser Val His Ile Leu Ser Ser Asp Pro Tyr
        435                 440                 445

Leu Trp Gln Phe Ala Asn Asp Pro Lys Phe Phe Leu Asn Glu Phe Asp
450                 455                 460

Leu Leu Gly Gln Ala Ala Ala Ser Lys Leu Ala Arg Asp Leu Thr Ser
465                 470                 475                 480

Gln Gly Ala Met Lys Glu Tyr Phe Ala Gly Glu Thr Leu Pro Gly Tyr
                485                 490                 495

Asn Leu Val Gln Asn Pro Thr Leu Ser Gln Trp Ser Asp Tyr Val Leu
            500                 505                 510

Gln Asn Phe Arg Pro Asn Trp His Ala Val Ser Ser Cys Ser Met Met
        515                 520                 525

Ser Arg Glu Leu Gly Gly Val Val Asp Ala Thr Ala Lys Val Tyr Gly
530                 535                 540

Thr Gln Gly Leu Arg Val Ile Asp Gly Ser Ile Pro Pro Thr Gln Val
545                 550                 555                 560

Ser Ser His Ser Met Thr Ile Phe Tyr Gly Met Ala Leu Lys Val Ala
                565                 570                 575

Asp Ala Ile Leu Asp Asp Tyr Ala Lys Ser Ala
            580                 585

<210> SEQ ID NO 11
<211> LENGTH: 33
<212> TYPE: DNA
<213> ORGANISM: Penicillium amagasakiense

<400> SEQUENCE: 11
ggtgtcttcc catgtcatga ccattttcta cgg                            33

<210> SEQ ID NO 12
<211> LENGTH: 33
<212> TYPE: DNA
<213> ORGANISM: Penicillium amagasakiense

<400> SEQUENCE: 12
ccgtagaaaa tggtcatgac atgggaagac acc                            33

<210> SEQ ID NO 13
<211> LENGTH: 33
<212> TYPE: DNA
<213> ORGANISM: Penicillium amagasakiense

<400> SEQUENCE: 13
ggtgtcttcc cattccatga ccattttcta cgg                            33

<210> SEQ ID NO 14
<211> LENGTH: 33
<212> TYPE: DNA
<213> ORGANISM: Penicillium amagasakiense

<400> SEQUENCE: 14
```

```
ccgtagaaaa tggtcatgga atgggaagac acc                                    33

<210> SEQ ID NO 15
<211> LENGTH: 33
<212> TYPE: DNA
<213> ORGANISM: Penicillium amagasakiense

<400> SEQUENCE: 15
ggtgtcttcc cataccatga ccattttcta cgg                                    33

<210> SEQ ID NO 16
<211> LENGTH: 33
<212> TYPE: DNA
<213> ORGANISM: Penicillium amagasakiense

<400> SEQUENCE: 16
ccgtagaaaa tggtcatggt atgggaagac acc                                    33

<210> SEQ ID NO 17
<211> LENGTH: 33
<212> TYPE: DNA
<213> ORGANISM: Penicillium amagasakiense

<400> SEQUENCE: 17
ggtgtcttcc catattatga ccattttcta cgg                                    33

<210> SEQ ID NO 18
<211> LENGTH: 33
<212> TYPE: DNA
<213> ORGANISM: Penicillium amagasakiense

<400> SEQUENCE: 18
ccgtagaaaa tggtcataat atgggaagac acc                                    33

<210> SEQ ID NO 19
<211> LENGTH: 26
<212> TYPE: DNA
<213> ORGANISM: Penicillium amagasakiense

<400> SEQUENCE: 19
ggacaccgag ggcgagatca acttcg                                            26

<210> SEQ ID NO 20
<211> LENGTH: 26
<212> TYPE: DNA
<213> ORGANISM: Penicillium amagasakiense

<400> SEQUENCE: 20
cgaagttgat ctcgccctcg gtgtcc                                            26

<210> SEQ ID NO 21
<211> LENGTH: 1769
<212> TYPE: DNA
<213> ORGANISM: Penicillium aculeatum

<400> SEQUENCE: 21
atgtacctgc ctgcccaaca gattgatgtc cagtctagtc ttctcagtga ccctagcaag       60
gttgcaggaa agacctatga ttacatcatt gctggtggtg gtttgactgg ccttactgtt      120
gctgccaaat tgacagaaaa ccccaagatc aaagtcctgg tcattgaaaa gggcttctat      180
gagtccaacg atggagccat catcgaggat ccaaatgctt atggacaaat ctttggcacc      240
actgttgacc agaactacct caccgttccc ctgatcaaca accgcacgaa caatatcaag      300
```

```
gccggtaaag gtcttggagg atcaaccttg ataaacggtg actcctggac tcgcccagac    360
aaagtccaga ttgattcttg ggagaaggtc tttggcatgg aaggttggaa ttgggacaac    420
atgttcgagt acatgaagaa ggccgaggct gcacgtaccc ctactgctgc tcagcttgct    480
gctggccact ccttcaatgc tacctgccat ggaaccaacg gtactgttca atccggagcc    540
cgtgacaacg gccagccttg gtctcctatt atgaaggccc ttatgaacac cgtctcggcc    600
cttggtgtcc ccgtacagca agactttctc tgtggtcatc cacgaggtgt ctctatgatc    660
atgaacaatc tcgacgaaaa ccaagttcgt gttgatgctg cccgtgcatg gctgcttccc    720
aactaccagc gctcgaattt ggagatcctt actggtcaga tggttggaaa ggttctgttt    780
aaacagaccg catccggtcc ccaggctgtt ggtgtgaact tcggtactaa taaggccgtc    840
aactttgacg tctttgctaa gcatgaggtc cttttggctg ctggctcagc tatctctccg    900
ctgatcttgg aatattctgg cataggcttg aagtctgttc ttgatcaagc caatgtcact    960
cagcttcttg atcttcctgt tggtatcaat atgcaagatc agaccacaac cactgtcagt   1020
tcccgtgcta gttccgctgg tgctggtcag ggtcaggccg tcttcttcgc caatttcact   1080
gagaccttcg gtgactacgc cccccaggcc agggacttac tcaacaccaa gctcgaccaa   1140
tgggccgagg agaccgttgc gcgcggtggt ttccataatg taactgctct caaagtacaa   1200
tacgaaaact atcgtaactg gctccttgac gaagacgtcg ccttcgccga gcttttcatg   1260
gacaccgagg ccagatcaa cttcgattta tgggatctca tcccctttcac tcgtggttcc   1320 gtccatatcc tcagtagcga tccttaccta tggcaattcg ccaacgaccc caaattcttc   1380
ctgaacgagt ttgacctcct tggtcaagct gccgcttcca gcttgctcg tgatctcact   1440 agccaaggcg ctatgaagga gtacttcgcc ggggagactc ttccaggata caacttggtc   1500
cagaatgcta ctctttccca gtggtcggat tatgtcttac agaacttccg tcccaactgg   1560
catgctgtga gcagctgctc tatgatgtct agagagcttg gtggtgtcgt tgatgctact   1620
gccaaggtgt acggtaccca aggcctacgt gtcattgacg gtctctattc ctccgactcag   1680 gtgtcttccc attccatgac cattttctac ggaatggctt tgaaggttgc tgatgccatt   1740
ttggatgact atgccaaaag tgcctcgct                                      1769
```

<210> SEQ ID NO 22
<211> LENGTH: 588
<212> TYPE: PRT
<213> ORGANISM: Penicillium amagasakiense

<400> SEQUENCE: 22

```
Tyr Leu Pro Ala Gln Gln Ile Asp Val Gln Ser Ser Leu Leu Ser Asp
1               5                   10                  15

Pro Ser Lys Val Ala Gly Lys Thr Tyr Asp Tyr Ile Ile Ala Gly Gly
                20                  25                  30

Gly Leu Thr Gly Leu Thr Val Ala Ala Lys Leu Thr Glu Asn Pro Lys
            35                  40                  45

Ile Lys Val Leu Val Ile Glu Lys Gly Phe Tyr Glu Ser Asn Asp Gly
        50                  55                  60

Ala Ile Ile Glu Asp Pro Asn Ala Tyr Gly Gln Ile Phe Gly Thr Thr
65                  70                  75                  80

Val Asp Gln Asn Tyr Leu Thr Val Pro Leu Ile Asn Asn Arg Thr Asn
                85                  90                  95

Asn Ile Lys Ala Gly Lys Gly Leu Gly Gly Ser Thr Leu Ile Asn Gly
                100                 105                 110
```

```
Asp Ser Trp Thr Arg Pro Asp Lys Val Gln Ile Asp Ser Trp Glu Lys
            115                 120                 125

Val Phe Gly Met Glu Gly Trp Asn Trp Asp Asn Met Phe Glu Tyr Met
130                 135                 140

Lys Lys Ala Glu Ala Ala Arg Thr Pro Thr Ala Ala Gln Leu Ala Ala
145                 150                 155                 160

Gly His Ser Phe Asn Ala Thr Cys His Gly Thr Asn Gly Thr Val Gln
                165                 170                 175

Ser Gly Ala Arg Asp Asn Gly Gln Pro Trp Ser Pro Ile Met Lys Ala
                180                 185                 190

Leu Met Asn Thr Val Ser Ala Leu Gly Val Pro Val Gln Gln Asp Phe
                195                 200                 205

Leu Cys Gly His Pro Arg Gly Val Ser Met Ile Met Asn Asn Leu Asp
        210                 215                 220

Glu Asn Gln Val Arg Val Asp Ala Ala Arg Ala Trp Leu Leu Pro Asn
225                 230                 235                 240

Tyr Gln Arg Ser Asn Leu Glu Ile Leu Thr Gly Gln Met Val Gly Lys
                245                 250                 255

Val Leu Phe Lys Gln Thr Ala Ser Gly Pro Gln Ala Val Gly Val Asn
                260                 265                 270

Phe Gly Thr Asn Lys Ala Val Asn Phe Asp Val Phe Ala Lys His Glu
            275                 280                 285

Val Leu Leu Ala Ala Gly Ser Ala Ile Ser Pro Leu Ile Leu Glu Tyr
290                 295                 300

Ser Gly Ile Gly Leu Lys Ser Val Leu Asp Gln Ala Asn Val Thr Gln
305                 310                 315                 320

Leu Leu Asp Leu Pro Val Gly Ile Asn Met Gln Asp Gln Thr Thr Thr
                325                 330                 335

Thr Val Ser Ser Arg Ala Ser Ser Ala Gly Ala Gly Gln Gly Gln Ala
            340                 345                 350

Val Phe Phe Ala Asn Phe Thr Glu Thr Phe Gly Asp Tyr Ala Pro Gln
            355                 360                 365

Ala Arg Asp Leu Leu Asn Thr Lys Leu Asp Gln Trp Ala Glu Glu Thr
            370                 375                 380

Val Ala Arg Gly Gly Phe His Asn Val Thr Ala Leu Lys Val Gln Tyr
385                 390                 395                 400

Glu Asn Tyr Arg Asn Trp Leu Leu Asp Glu Asp Val Ala Phe Ala Glu
                405                 410                 415

Leu Phe Met Asp Thr Glu Gly Gln Ile Asn Phe Asp Leu Trp Asp Leu
                420                 425                 430

Ile Pro Phe Thr Arg Gly Ser Val His Ile Leu Ser Ser Asp Pro Tyr
            435                 440                 445

Leu Trp Gln Phe Ala Asn Asp Pro Lys Phe Phe Leu Asn Glu Phe Asp
        450                 455                 460

Leu Leu Gly Gln Ala Ala Ala Ser Lys Leu Ala Arg Asp Leu Thr Ser
465                 470                 475                 480

Gln Gly Ala Met Lys Glu Tyr Phe Ala Gly Glu Thr Leu Pro Gly Tyr
                485                 490                 495

Asn Leu Val Gln Asn Ala Thr Leu Ser Gln Trp Ser Asp Tyr Val Leu
                500                 505                 510

Gln Asn Phe Arg Pro Asn Trp His Ala Val Ser Ser Cys Ser Met Met
            515                 520                 525
```

Ser Arg Glu Leu Gly Gly Val Val Asp Ala Thr Ala Lys Val Tyr Gly
    530                 535                 540

Thr Gln Gly Leu Arg Val Ile Asp Gly Ser Ile Pro Pro Thr Gln Val
545                 550                 555                 560

Ser Ser His Ser Met Thr Ile Phe Tyr Gly Met Ala Leu Lys Val Ala
                565                 570                 575

Asp Ala Ile Leu Asp Asp Tyr Ala Lys Ser Ala Ser
            580                 585

<210> SEQ ID NO 23
<211> LENGTH: 1769
<212> TYPE: DNA
<213> ORGANISM: Penicillium amagasakiense

<400> SEQUENCE: 23

| | | | | | |
|---|---|---|---|---|---|
| atgtacctgc | ctgcccaaca | gattgatgtc | cagtctagtc | ttctcagtga | ccctagcaag | 60 |
| gttgcaggaa | agacctatga | ttacatcatt | gctggtggtg | gtttgactgg | ccttactgtt | 120 |
| gctgccaaat | tgacagaaaa | ccccaagatc | aaagtcctgg | tcattgaaaa | gggcttctat | 180 |
| gagtccaacg | atggagccat | catcgaggat | ccaaatgctt | atggacaaat | ctttggcacc | 240 |
| actgttgacc | agaactacct | caccgttccc | ctgatcaaca | accgcacgaa | caatatcaag | 300 |
| gccggtaaag | gtcttggagg | atcaaccttg | ataaacggtg | actcctggac | tcgcccagac | 360 |
| aaagtccaga | ttgattcttg | ggagaaggtc | tttggcatgg | aaggttggaa | ttgggacaac | 420 |
| atgttcgagt | acatgaagaa | ggccgaggct | gcacgtaccc | ctactgctgc | tcagcttgct | 480 |
| gctggccact | ccttcaatgc | tacctgccat | ggaaccaacg | gtactgttca | atccggagcc | 540 |
| cgtgacaacg | gccagccttg | gtctcctatt | atgaaggccc | ttatgaacac | cgtctcggcc | 600 |
| cttggtgtcc | ccgtacagca | agactttctc | tgtggtcatc | cacgaggtgt | ctctatgatc | 660 |
| atgaacaatc | tcgacgaaaa | ccaagttcgt | gttgatgctg | cccgtgcatg | gctgcttccc | 720 |
| aactaccagc | gctcgaattt | ggagatcctt | actggtcaga | tggttggaaa | ggttctgttt | 780 |
| aaacagaccg | catccggtcc | ccaggctgtt | ggtgtgaact | tcggtactaa | taggccgtc | 840 |
| aactttgacg | tctttgctaa | gcatgaggtc | cttttggctg | ctggctcagc | tatctctccg | 900 |
| ctgatcttgg | aatattctgg | cataggcttg | aagtctgttc | ttgatcaagc | caatgtcact | 960 |
| cagcttcttg | atcttcctgt | tggtatcaat | atgcaagatc | agaccacaac | cactgtcagt | 1020 |
| tcccgtgcta | gttccgctgg | tgctggtcag | ggtcaggccg | tcttcttcgc | caatttcact | 1080 |
| gagaccttcg | gtgactacgc | cccccaggcc | agggacttac | tcaacaccaa | gctcgaccaa | 1140 |
| tgggccgagg | agaccgttgc | gcgcggtggt | ttccataatg | taactgctct | caaagtacaa | 1200 |
| tacgaaaact | atcgtaactg | gctccttgac | gaagacgtcg | ccttcgccga | gcttttcatg | 1260 |
| gacaccgagg | gcatgatcaa | cttcgattta | tgggatctca | tccctttcac | tcgtggttcc | 1320 |
| gtccatatcc | tcagtagcga | tccttaccta | tggcaattcg | ccaacgaccc | caaattcttc | 1380 |
| ctgaacgagt | ttgacctcct | tggtcaagct | gccgcttcca | agcttgctcg | tgatctcact | 1440 |
| agccaaggcg | ctatgaagga | gtacttcgcc | ggggagactc | ttccaggata | caacttggtc | 1500 |
| cagaatgcta | ctcttttccca | gtggtcggat | tatgtcttac | agaacttccg | tcccaactgg | 1560 |
| catgctgtga | gcagctgctc | tatgatgtct | agagagcttg | gtggtgtcgt | tgatgctact | 1620 |
| gccaaggtgt | acggtaccca | aggcctacgt | gtcattgacg | gtctattcc | tccgactcag | 1680 |
| gtgtcttccc | attccatgac | catttttctac | ggaatggctt | tgaaggttgc | tgatgccatt | 1740 |
| ttggatgact | atgccaaaag | tgcctcgct | | | | 1769 |

<210> SEQ ID NO 24
<211> LENGTH: 588
<212> TYPE: PRT
<213> ORGANISM: Penicillium amagasakiense

<400> SEQUENCE: 24

```
Tyr Leu Pro Ala Gln Gln Ile Asp Val Gln Ser Ser Leu Leu Ser Asp
1               5                   10                  15

Pro Ser Lys Val Ala Gly Lys Thr Tyr Asp Tyr Ile Ile Ala Gly Gly
            20                  25                  30

Gly Leu Thr Gly Leu Thr Val Ala Ala Lys Leu Thr Glu Asn Pro Lys
        35                  40                  45

Ile Lys Val Leu Val Ile Glu Lys Gly Phe Tyr Glu Ser Asn Asp Gly
50                  55                  60

Ala Ile Ile Glu Asp Pro Asn Ala Tyr Gly Gln Ile Phe Gly Thr Thr
65                  70                  75                  80

Val Asp Gln Asn Tyr Leu Thr Val Pro Leu Ile Asn Asn Arg Thr Asn
                85                  90                  95

Asn Ile Lys Ala Gly Lys Gly Leu Gly Gly Ser Thr Leu Ile Asn Gly
            100                 105                 110

Asp Ser Trp Thr Arg Pro Asp Lys Val Gln Ile Asp Ser Trp Glu Lys
        115                 120                 125

Val Phe Gly Met Glu Gly Trp Asn Trp Asp Asn Met Phe Glu Tyr Met
130                 135                 140

Lys Lys Ala Glu Ala Ala Arg Thr Pro Thr Ala Ala Gln Leu Ala Ala
145                 150                 155                 160

Gly His Ser Phe Asn Ala Thr Cys His Gly Thr Asn Gly Thr Val Gln
                165                 170                 175

Ser Gly Ala Arg Asp Asn Gly Gln Pro Trp Ser Pro Ile Met Lys Ala
            180                 185                 190

Leu Met Asn Thr Val Ser Ala Leu Gly Val Pro Val Gln Gln Asp Phe
        195                 200                 205

Leu Cys Gly His Pro Arg Gly Val Ser Met Ile Met Asn Asn Leu Asp
210                 215                 220

Glu Asn Gln Val Arg Val Asp Ala Ala Arg Ala Trp Leu Leu Pro Asn
225                 230                 235                 240

Tyr Gln Arg Ser Asn Leu Glu Ile Leu Thr Gly Gln Met Val Gly Lys
                245                 250                 255

Val Leu Phe Lys Gln Thr Ala Ser Gly Pro Gln Ala Val Gly Val Asn
            260                 265                 270

Phe Gly Thr Asn Lys Ala Val Asn Phe Asp Val Phe Ala Lys His Glu
        275                 280                 285

Val Leu Leu Ala Ala Gly Ser Ala Ile Ser Pro Leu Ile Leu Glu Tyr
290                 295                 300

Ser Gly Ile Gly Leu Lys Ser Val Leu Asp Gln Ala Asn Val Thr Gln
305                 310                 315                 320

Leu Leu Asp Leu Pro Val Gly Ile Asn Met Gln Asp Gln Thr Thr Thr
                325                 330                 335

Thr Val Ser Ser Arg Ala Ser Ser Ala Gly Ala Gly Gln Gly Gln Ala
            340                 345                 350

Val Phe Phe Ala Asn Phe Thr Glu Thr Phe Gly Asp Tyr Ala Pro Gln
        355                 360                 365

Ala Arg Asp Leu Leu Asn Thr Lys Leu Asp Gln Trp Ala Glu Glu Thr
```

```
                370                 375                 380
Val Ala Arg Gly Gly Phe His Asn Val Thr Ala Leu Lys Val Gln Tyr
385                 390                 395                 400

Glu Asn Tyr Arg Asn Trp Leu Leu Asp Glu Asp Val Ala Phe Ala Glu
                405                 410                 415

Leu Phe Met Asp Thr Glu Gly Met Ile Asn Phe Asp Leu Trp Asp Leu
                420                 425                 430

Ile Pro Phe Thr Arg Gly Ser Val His Ile Leu Ser Ser Asp Pro Tyr
                435                 440                 445

Leu Trp Gln Phe Ala Asn Asp Pro Lys Phe Phe Leu Asn Glu Phe Asp
                450                 455                 460

Leu Leu Gly Gln Ala Ala Ala Ser Lys Leu Ala Arg Asp Leu Thr Ser
465                 470                 475                 480

Gln Gly Ala Met Lys Glu Tyr Phe Ala Gly Glu Thr Leu Pro Gly Tyr
                485                 490                 495

Asn Leu Val Gln Asn Ala Thr Leu Ser Gln Trp Ser Asp Tyr Val Leu
                500                 505                 510

Gln Asn Phe Arg Pro Asn Trp His Ala Val Ser Ser Cys Ser Met Met
                515                 520                 525

Ser Arg Glu Leu Gly Gly Val Val Asp Ala Thr Ala Lys Val Tyr Gly
                530                 535                 540

Thr Gln Gly Leu Arg Val Ile Asp Gly Ser Ile Pro Pro Thr Gln Val
545                 550                 555                 560

Ser Ser His Ser Met Thr Ile Phe Tyr Gly Met Ala Leu Lys Val Ala
                565                 570                 575

Asp Ala Ile Leu Asp Asp Tyr Ala Lys Ser Ala Ser
                580                 585

<210> SEQ ID NO 25
<211> LENGTH: 1769
<212> TYPE: DNA
<213> ORGANISM: Penicillium amagasakiense

<400> SEQUENCE: 25
atgtacctgc ctgcccaaca gattgatgtc cagtctagtc ttctcagtga ccctagcaag      60
gttgcaggaa agacctatga ttacatcatt gctggtggtg gtttgactgg ccttactgtt     120
gctgccaaat tgacagaaaa ccccaagatc aaagtcctgg tcattgaaaa gggcttctat     180
gagtccaacg atggagccat catcgaggat ccaaatgctt atggacaaat ctttggcacc     240
actgttgacc agaactacct caccgttccc ctgatcaaca accgcacgaa caatatcaag     300
gccggtaaag gtcttggagg atcaaccttg ataaacggtg actcctggac tcgcccagac     360
aaagtccaga ttgattcttg ggagaaggtc tttggcatgg aaggttggaa ttgggacaac     420
atgttcgagt acatgaagaa ggccgaggct gcacgtaccc ctactgctgc tcagcttgct     480
gctggccact ccttcaatgc tacctgccat ggaaccaacg tactgttca atccggagcc     540 cgtgacaacg gccagccttg gtctcctatt atgaaggccc ttatgaacac cgtctcggcc     600
cttggtgtcc ccgtacagca agactttctc tgtggtcatc cacgaggtgt ctctatgatc     660
atgaacaatc tcgacgaaaa ccaagttcgt gttgatgctg cccgtgcatg gctgcttccc     720
aactaccagc gctcgaattt ggagatcctt actggtcaga tggttggaaa ggttctgttt     780
aaacagaccg catccggtcc ccaggctgtt ggtgtgaact tcggtactaa taaggccgtc     840
aactttgacg tctttgctaa gcatgaggtc cttttggctg ctggctcagc tatctctccg     900
```

```
ctgatcttgg aatattctgg cataggcttg aagtctgttc ttgatcaagc caatgtcact    960
cagcttcttg atcttcctgt tggtatcaat atgcaagatc agaccacaac cactgtcagt   1020
tcccgtgcta gttccgctgg tgctggtcag ggtcaggccg tcttcttcgc caatttcact   1080
gagaccttcg gtgactacgc cccccaggcc agggacttac tcaacaccaa gctcgaccaa   1140
tgggccgagg agaccgttgc gcgcggtggt ttccataatg taactgctct caaagtacaa   1200
tacgaaaact atcgtaactg gctccttgac gaagacgtcg ccttcgccga gcttttcatg   1260
gacaccgagg gcttgatcaa cttcgattta tgggatctca tcccttttcac tcgtggttcc   1320
gtccatatcc tcagtagcga tccttaccta tggcaattcg ccaacgaccc caaattcttc   1380
ctgaacgagt ttgacctcct tggtcaagct gccgcttcca gcttgctcg tgatctcact   1440
agccaaggcg ctatgaagga gtacttcgcc ggggagactc ttccaggata caacttggtc   1500
cagaatgcta ctcttttccca gtggtcggat tatgtcttac agaacttccg tcccaactgg   1560
catgctgtga gcagctgctc tatgatgtct agagagcttg gtggtgtcgt tgatgctact   1620
gccaaggtgt acggtaccca aggcctacgt gtcattgacg gtctattcc tccgactcag   1680
gtgtcttccc attccatgac cattttctac ggaatggctt tgaaggttgc tgatgccatt   1740
ttggatgact atgccaaaag tgcctcgct                                    1769
```

<210> SEQ ID NO 26
<211> LENGTH: 588
<212> TYPE: PRT
<213> ORGANISM: Penicillium amagasakiense

<400> SEQUENCE: 26

```
Tyr Leu Pro Ala Gln Gln Ile Asp Val Gln Ser Ser Leu Leu Ser Asp
1               5                   10                  15

Pro Ser Lys Val Ala Gly Lys Thr Tyr Asp Tyr Ile Ile Ala Gly Gly
            20                  25                  30

Gly Leu Thr Gly Leu Thr Val Ala Ala Lys Leu Thr Glu Asn Pro Lys
        35                  40                  45

Ile Lys Val Leu Val Ile Glu Lys Gly Phe Tyr Glu Ser Asn Asp Gly
    50                  55                  60

Ala Ile Ile Glu Asp Pro Asn Ala Tyr Gly Gln Ile Phe Gly Thr Thr
65                  70                  75                  80

Val Asp Gln Asn Tyr Leu Thr Val Pro Leu Ile Asn Asn Arg Thr Asn
                85                  90                  95

Asn Ile Lys Ala Gly Lys Gly Leu Gly Gly Ser Thr Leu Ile Asn Gly
            100                 105                 110

Asp Ser Trp Thr Arg Pro Asp Lys Val Gln Ile Asp Ser Trp Glu Lys
        115                 120                 125

Val Phe Gly Met Glu Gly Trp Asn Trp Asp Asn Met Phe Glu Tyr Met
    130                 135                 140

Lys Lys Ala Glu Ala Ala Arg Thr Pro Thr Ala Ala Gln Leu Ala Ala
145                 150                 155                 160

Gly His Ser Phe Asn Ala Thr Cys His Gly Thr Asn Gly Thr Val Gln
                165                 170                 175

Ser Gly Ala Arg Asp Asn Gly Gln Pro Trp Ser Pro Ile Met Lys Ala
            180                 185                 190

Leu Met Asn Thr Val Ser Ala Leu Gly Val Pro Val Gln Gln Asp Phe
        195                 200                 205

Leu Cys Gly His Pro Arg Gly Val Ser Met Ile Met Asn Asn Leu Asp
    210                 215                 220
```

```
Glu Asn Gln Val Arg Val Asp Ala Ala Arg Ala Trp Leu Leu Pro Asn
225                 230                 235                 240

Tyr Gln Arg Ser Asn Leu Glu Ile Leu Thr Gly Gln Met Val Gly Lys
            245                 250                 255

Val Leu Phe Lys Gln Thr Ala Ser Gly Pro Gln Ala Val Gly Val Asn
        260                 265                 270

Phe Gly Thr Asn Lys Ala Val Asn Phe Asp Val Phe Ala Lys His Glu
            275                 280                 285

Val Leu Leu Ala Ala Gly Ser Ala Ile Ser Pro Leu Ile Leu Glu Tyr
        290                 295                 300

Ser Gly Ile Gly Leu Lys Ser Val Leu Asp Gln Ala Asn Val Thr Gln
305                 310                 315                 320

Leu Leu Asp Leu Pro Val Gly Ile Asn Met Gln Asp Gln Thr Thr Thr
                325                 330                 335

Thr Val Ser Ser Arg Ala Ser Ser Ala Gly Ala Gly Gln Gly Gln Ala
            340                 345                 350

Val Phe Phe Ala Asn Phe Thr Glu Thr Phe Gly Asp Tyr Ala Pro Gln
        355                 360                 365

Ala Arg Asp Leu Leu Asn Thr Lys Leu Asp Gln Trp Ala Glu Glu Thr
            370                 375                 380

Val Ala Arg Gly Gly Phe His Asn Val Thr Ala Leu Lys Val Gln Tyr
385                 390                 395                 400

Glu Asn Tyr Arg Asn Trp Leu Leu Asp Glu Asp Val Ala Phe Ala Glu
                405                 410                 415

Leu Phe Met Asp Thr Glu Gly Leu Ile Asn Phe Asp Leu Trp Asp Leu
            420                 425                 430

Ile Pro Phe Thr Arg Gly Ser Val His Ile Leu Ser Ser Asp Pro Tyr
        435                 440                 445

Leu Trp Gln Phe Ala Asn Asp Pro Lys Phe Phe Leu Asn Glu Phe Asp
        450                 455                 460

Leu Leu Gly Gln Ala Ala Ala Ser Lys Leu Ala Arg Asp Leu Thr Ser
465                 470                 475                 480

Gln Gly Ala Met Lys Glu Tyr Phe Ala Gly Glu Thr Leu Pro Gly Tyr
                485                 490                 495

Asn Leu Val Gln Asn Ala Thr Leu Ser Gln Trp Ser Asp Tyr Val Leu
            500                 505                 510

Gln Asn Phe Arg Pro Asn Trp His Ala Val Ser Ser Cys Ser Met Met
        515                 520                 525

Ser Arg Glu Leu Gly Gly Val Val Asp Ala Thr Ala Lys Val Tyr Gly
530                 535                 540

Thr Gln Gly Leu Arg Val Ile Asp Gly Ser Ile Pro Pro Thr Gln Val
545                 550                 555                 560

Ser Ser His Ser Met Thr Ile Phe Tyr Gly Met Ala Leu Lys Val Ala
            565                 570                 575

Asp Ala Ile Leu Asp Asp Tyr Ala Lys Ser Ala Ser
            580                 585

<210> SEQ ID NO 27
<211> LENGTH: 33
<212> TYPE: DNA
<213> ORGANISM: Penicillium amagasakiense

<400> SEQUENCE: 27
ggacaccgag ggccagatca acttcgattt atg                          33
```

```
<210> SEQ ID NO 28
<211> LENGTH: 33
<212> TYPE: DNA
<213> ORGANISM: Penicillium amagasakiense

<400> SEQUENCE: 28
cataaatcga agttgatctg gccctcggtg tcc                                33

<210> SEQ ID NO 29
<211> LENGTH: 33
<212> TYPE: DNA
<213> ORGANISM: Penicillium amagasakiense

<400> SEQUENCE: 29
ggacaccgag ggcatgatca acttcgattt atg                                33

<210> SEQ ID NO 30
<211> LENGTH: 33
<212> TYPE: DNA
<213> ORGANISM: Penicillium amagasakiense

<400> SEQUENCE: 30
cataaatcga agttgatcat gccctcggtg tcc                                33

<210> SEQ ID NO 31
<211> LENGTH: 33
<212> TYPE: DNA
<213> ORGANISM: Penicillium amagasakiense

<400> SEQUENCE: 31
ggacaccgag ggcttgatca acttcgattt atg                                33

<210> SEQ ID NO 32
<211> LENGTH: 33
<212> TYPE: DNA
<213> ORGANISM: Penicillium amagasakiense

<400> SEQUENCE: 32
cataaatcga agttgatcaa gccctcggtg tcc                                33
```